(12) United States Patent
Ragini et al.

(10) Patent No.: US 7,670,692 B2
(45) Date of Patent: Mar. 2, 2010

(54) CYCLOMETALATED TRANSITION METAL COMPLEX AND ORGANIC ELECTROLUMINESCENT DEVICE USING THE SAME

(75) Inventors: Das Rupasree Ragini, Suwon-si (KR); Seok Chang, Daejeon-si (KR); Eun-Sil Han, Yongin-si (KR); Hee-Kyung Kim, Anyang-si (KR); Lyong-Sun Pu, Suwon-si (KR); Jong-Hyoup Lee, Seoul (KR)

(73) Assignee: Samsung Mobile Display Co., Ltd., Giheung-Gu, Youngin, Gyunggi-Do (KR)

( * ) Notice: Subject to any disclaimer, the term of this patent is extended or adjusted under 35 U.S.C. 154(b) by 741 days.

(21) Appl. No.: 11/347,242

(22) Filed: Feb. 6, 2006

(65) Prior Publication Data
US 2006/0177695 A1 Aug. 10, 2006

(30) Foreign Application Priority Data
Feb. 4, 2005 (KR) .................. 10-2005-0010857

(51) Int. Cl.
*H01L 51/54* (2006.01)
*C09K 11/06* (2006.01)

(52) U.S. Cl. .................. 428/690; 428/917; 313/504; 313/506; 257/40; 257/E51.044; 548/101; 548/103; 548/110; 546/4; 546/10

(58) Field of Classification Search .................. 428/690, 428/917; 313/504, 506; 257/40, E51.044; 548/101, 103, 108, 110
See application file for complete search history.

(56) References Cited

U.S. PATENT DOCUMENTS

| 6,926,883 | B1 * | 8/2005 | Dyszlewski et al. ......... 424/1.65 |
| 2002/0025419 | A1 * | 2/2002 | Lee et al. .................... 428/212 |
| 2002/0064681 | A1 | 5/2002 | Takiguchi et al. |
| 2002/0134984 | A1 | 9/2002 | Igarashi |
| 2002/0182441 | A1 | 12/2002 | Lamansky et al. |
| 2005/0112406 | A1 * | 5/2005 | Han et al. ................... 428/690 |
| 2006/0124902 | A1 * | 6/2006 | Ziegler ........................ 252/364 |

FOREIGN PATENT DOCUMENTS

WO  WO 02/15645  2/2002

OTHER PUBLICATIONS

Gutierrez et al. "Organometallic derivatives of Ni(II) with poly(pyrazolyl)borate ligands." J. Organomet. Chem. 1998. vol. 551, pp. 215-227.*
Fieser and Fieser, Organic Chemistry, 1956, Reinhold, 3rd Edition, pp. 802-803.*
M. A. Baldo et al., "Highly efficient phosphorescent emission from organic electroluminescent devices", Nature, vol. 395, Sep. 10, 1998, pp. 151-154.

* cited by examiner

*Primary Examiner*—D. Lawrence Tarazano
*Assistant Examiner*—Michael Wilson
(74) *Attorney, Agent, or Firm*—Robert E. Bushnell, Esq.

(57) ABSTRACT

A cyclometalated transition metal complex very efficiently emits phosphorescent light and an organic electroluminescent device using the same. The transition metal complex is suitable for an organic layer of an organic electroluminescent device, can emit light with a wavelength of 400 to 650 nm, and can emit white light when used with a red emissive material or a green emissive material.

20 Claims, 7 Drawing Sheets

CYCLOMETALATED TRANSITION METAL COMPLEX AND ORGANIC ELECTROLUMINESCENT DEVICE USING THE SAME

CROSS-REFERENCE TO RELATED PATENT APPLICATIONS AND CLAIM OF PRIORITY

This application claims the benefit of Korean Patent Application No. 10-2005-0010857, filed on Feb. 4, 2005, in the Korean Intellectual Property Office, the disclosure of which is incorporated herein in its entirety by reference.

BACKGROUND OF THE INVENTION

1. Field of the Invention

The present invention relates to a cyclometalated transition metal complex and an organic electroluminescent device using the same, and more particularly, to a cyclometalated transition metal complex that can emit light ranging from a blue wavelength region to a red wavelength region through triplet metal-to-ligand charge-transfer (MLCT) and an organic electroluminescent device including an organic layer composed of the cyclometalated transition metal complex.

2. Description of the Related Art

Organic electroluminescent (EL) devices, which are active display devices, use the recombination of electrons and holes occurring in a fluorescent or phosphorescent organic layer when current is applied to emit light. Organic EL devices are lightweight, have wide viewing angles, produce high-quality images, and can be manufactured using simple processes. Organic EL devices can produce moving images with high color purity with low consumption power and low voltage. Accordingly, organic EL devices are suitable for portable electronic applications.

In general, an organic EL device includes an anode, a hole transport layer, an emission layer, an electron transport layer, and a cathode stacked sequentially on a substrate. The hole transport layer, the emission layer, and the electron transport layer are organic layers. The organic EL device may operate thorough the following mechanism. First, voltage is provided between the anode and the cathode. Holes injected from the anode move to the emission layer through the hole transport layer, and electrons injected from the cathode move to the emission layer through the electron transport layer. In the emission layer, the holes and electrons are recombined, thus producing excitons. The excitons decay radiatively, emitting light corresponding to the band gap of a material.

Materials for forming an emission layer are divided into fluorescent materials using singlet-state excitons and phosphorescent materials using triplet-state excitons, according to emission mechanism. The fluorescent material or phosphorescent material may form the emission layer, or a fluorescent or phosphorescent material-doped host material may form the emission layer. When electrons are excited, singlet excitons and triplet excitons are generated in a stastics ratio of 1:3.

When an emission layer is composed of the fluorescent material, triplet excitons that are generated in the host cannot be used. On the other hand, when an emission layer is composed of the phosphorescent material, both singlet excitons and triplet excitons can be used, and thus, an inner quantum efficiency of 100% can be obtained (see Baldo et al., Nature, Vol. 395, 151-154, 1998). Accordingly, the use of phosphorescent material results in higher luminance efficiency than the fluorescent material.

When an organic molecule contains a heavy metal, such as Ir, Pt, Rh, or Pd, spin-orbital coupling occurs due to a heavy atom effect, and thus, singlet states and triplet states are mixed, allowing a forbidden transition to occur and thus effectively emitting phosphorescent light even at room temperature.

Recently, highly efficient green and red emissive materials that use phosphorescence having the inner quantum efficiency of 100% have been developed.

For example, transition metal compounds that include a transition metal such as Ir or Pt have been developed. However, materials that are suitable for highly effective full-color display and low power consumption fluorescent applications are green and red emissive materials only. In other words, blue phosphorescent emissive materials have not been developed. Accordingly, a phosphorescent full-color device cannot be manufactured.

In order to resolve this problem, blue emissive materials (disclosed in WO 02/15645 A1 and US 2002/0064681 A1); cyclometalated transition metal complexes that contain a bulky functional group that can deform the molecular geometry for widening the gap between a highest occupied molecular orbital (HOMO) and a lowest unoccupied molecular orbital (LUMO) or a functional group with a high ligand field such as a cyano group (disclosed in Mat. Res. Soc. Symp. Proc. 708, 119, 2002; and 3rd Chitose International Forum on Photonics Science and Technology, Chitose, Japan, 6-8 Oct. 2002.); an Ir complex, such as $Ir(ppy)_2P(ph)_3Y$ where Y=Cl or CN (disclosed in US 2002/0182441 A1); and an Ir (III) complex containing a cyclometalating ligand, chelating diphosphine, Cl, and a cyano group (disclosed in US 2002/0048689 A1) have been developed.

In addition, US Patent Publication No. 2002-0134984 discloses a cyclometalated transition metal complex containing nitrogen and carbon and an organic EL device using the same.

However, none of these blue emissive materials simultaneously have desired color purities, luminance efficiencies, and lifetimes.

SUMMARY OF THE INVENTION

The present invention provides a cyclometalated transition metal complex that can effectively emit light ranging from a blue wavelength region to a red wavelength region through a triplet metal-to-ligand charge-transfer (MLCT).

The present invention also provides an organic electroluminescent device that can efficiently emit light ranging from a blue wavelength region to a red wavelength region.

According to an aspect of the present invention, there is provided a cyclometalated transition metal complex represented by Formula 1:

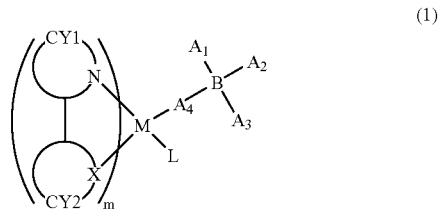

(1)

where M is a transition metal;
X is N or C;
L is a neutral ligand;
CY1 and CY2 are each independently an aromatic or aliphatic ring system;
m is 1 or 2;

A4 is imidazole, pyrazole, or derivatives thereof; and $A_1$, $A_2$, and $A_3$ are each independently a hydrogen atom, imidazole, pyrazole, or derivatives thereof.

According to another aspect of the present invention, there is provided an organic electroluminescent device including an organic layer interposed between a pair of electrodes, the organic layer comprising the cyclometalated transition metal complex represented by Formula 1.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
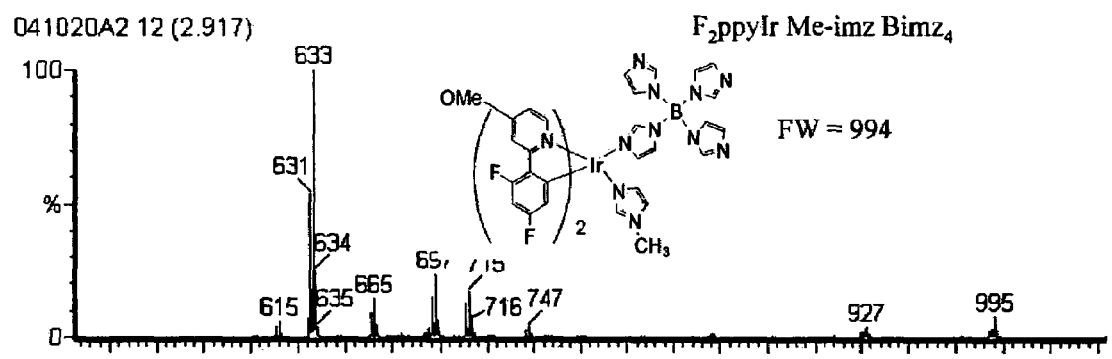
FIG. 1 illustrates a mass spectrum of a compound according to Example 1.
Figure 2:
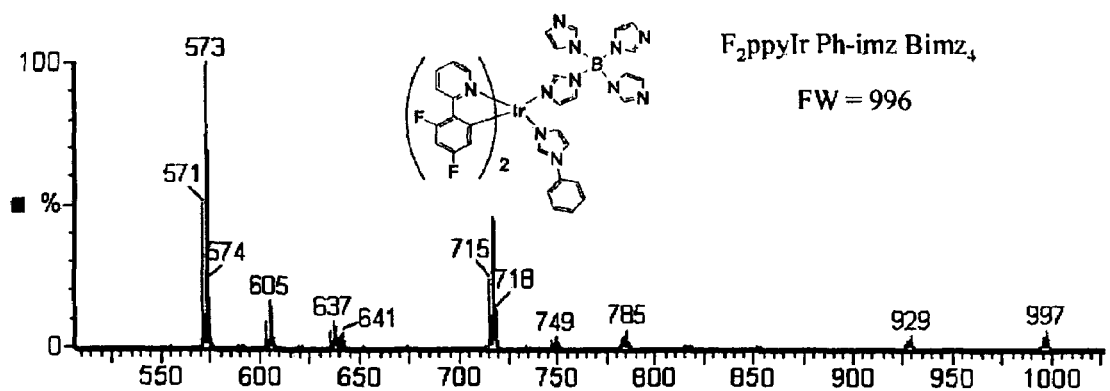
FIG. 2 illustrates a mass spectrum of a compound according to Example 3.
Figure 3:
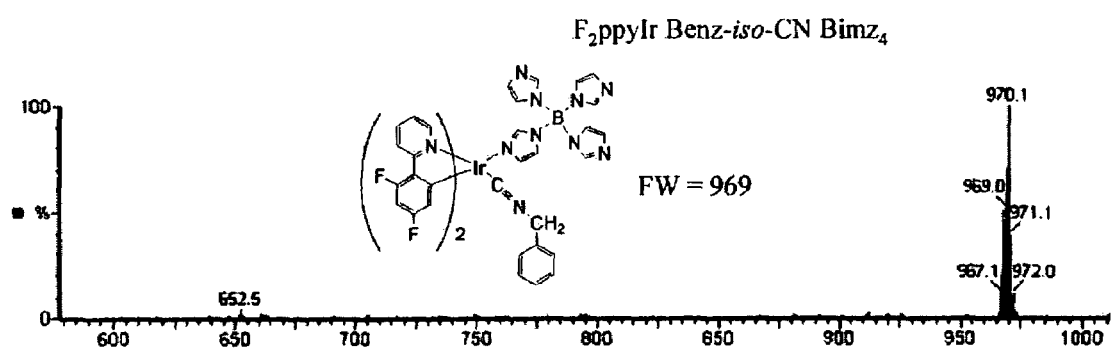
FIG. 3 illustrates a mass spectrum of a compound according to Example 4.
Figure 4:
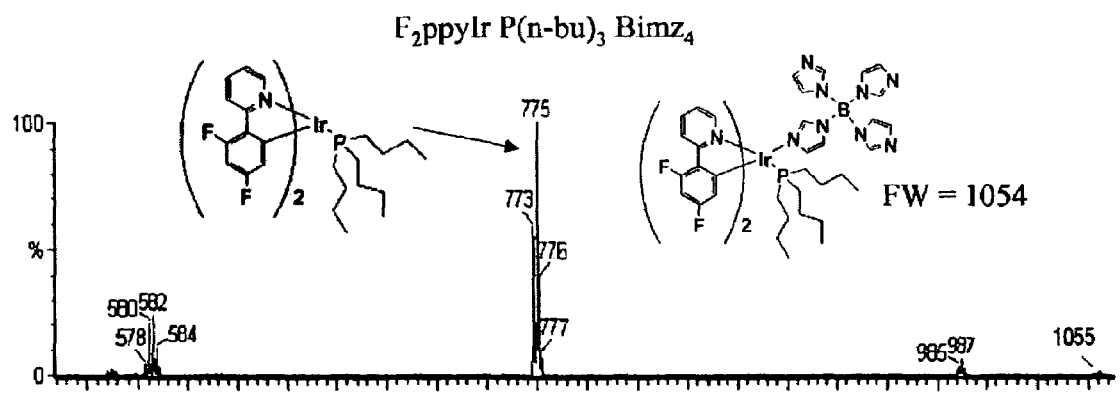
FIG. 4 illustrates a mass spectrum of a compound according to Example 5.

A cyclometalated transition metal complex according to an embodiment of the present invention is suitable for efficient blue emission with high performance because it contains a non-carbon coordinating chelating ligand.

A cyclometalated transition metal complex according to an embodiment of the present invention may be represented by Formula 1:

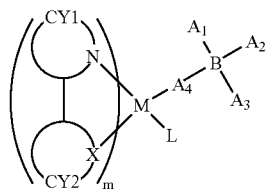

(1)

where M is a transition metal;

X is N or C;

L is a neutral ligand;

CY1 and CY2 are each independently an aromatic or aliphatic ring system;

m is 1 or 2;

$A_4$ is imidazole, pyrazole, or derivatives thereof; and $A_1$, $A_2$, and $A_3$ are each independently a hydrogen atom, imidazole, pyrazole, or derivatives thereof.

CY1 contains a nitrogen atom that can be bonded to M, and CY2 contains X (i.e., N or C) that can be bonded to M.

CY1-CY2 (i.e., the group shown in the parentheses of Formula 1) formed by CY1 and CY2 is a cyclometalating ligand that is bonded to M through N and X.

The cyclometalated transition metal complex of Formula 1 may be represented by one of Formulae 2 through 4:

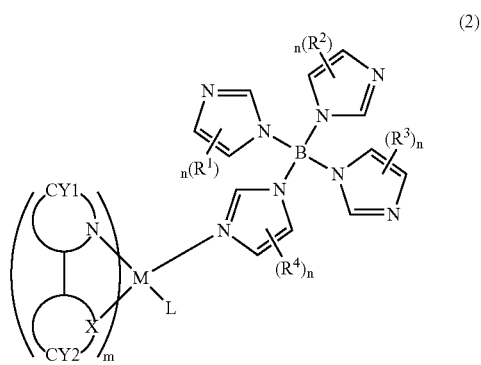

(2)

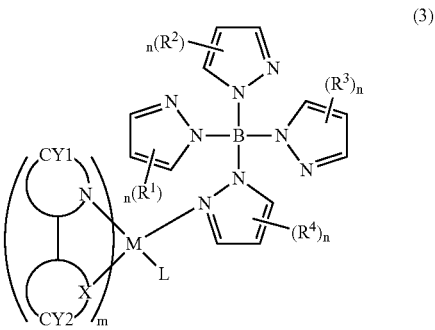

(3)

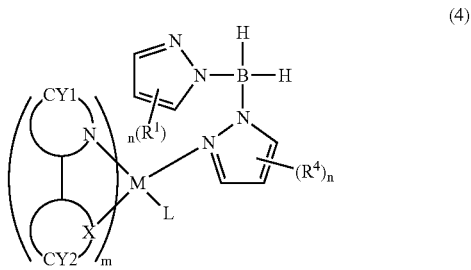

(4)

where M is a transition metal;

X is N or C;

L is a neutral ligand;

CY1 and CY2 are each independently an aromatic or aliphatic ring system;

m is 1 or 2;

$R^1$, $R^2$, $R^3$, and $R^4$ are each independently a substituent or H; and n is 1, 2, or 3.

The cyclometalated transition metal complex represented by Formula 2 contains a boron imidazolate ligand bonded to the transition metal, and the cyclometalated transition metal complexes represented by Formula 3 or Formula 4 contain a boron pyrazolate ligand bonded to the transition metal.

Preferably, in Formula 1, $A_1$, $A_2$, $A_3$, and A4 can each independently be an imidazole or pyrazole substituted with a compound selected from an alkyl group (for example, a C1-C30 alkyl group, preferably, a C1-C20 alkyl group, more preferably, a C1-C10 alkyl group), an alkenyl group (for example, a C2-C30 alkenyl group, preferably, a C2-C20 alkenyl group, more preferably, a C2-C10 alkenyl group), an alkynyl group (for example, a C2-C30 alkynyl group, preferably, a C2-C20 alkynyl group, more preferably, a C2-C10 alkynyl group), an aryl group (for example, a C6-C30 aryl group, preferably, a C6-C20 aryl group, more preferably, a C6-C12 aryl group), an amino group (for example, a C0-C30 amino group, preferably, a C0-C20 amino group, more preferably, a C0-C10 amino group), an alkoxy group (for example, a C1-C30 alkoxy group, preferably, a C1-C20 alkoxy group, more preferably, a C1-C10 alkoxy group), an aryloxy group (for example, a C6-C30 aryloxy group, preferably, a C6-C20 aryloxy group, more preferably, a C6-C12 aryloxy group), a heterocyclicoxy group (for example, a C1-C30 heterocyclicoxy group, preferably, a C1-C20 heterocyclicoxy group, more preferably, a C1-C12 heterocyclicoxy group), an acyl group (for example, a C1-C30 acyl group, preferably, a C1-C20 acyl group, more preferably, a C1-C12 acyl group), an alkoxycarbonyl group (for example, a C2-C30 alkoxycarbonyl group, preferably, a C2-C20 alkoxycarbonyl group, more preferably, a C2-C12 alkoxycarbonyl group), an aryloxycarbonyl group (for example, a C7-C30 aryloxycarbonyl group, preferably, a C7-C20 aryloxycarbonyl group, more preferably, a C7-C12 aryloxycarbonyl group), an acyloxy group (for example, a C2-C30 acyloxy group, preferably, a C2-C20 acyloxy group, more preferably, a C2-C10 acyloxy group), an acylamino group (for example, a C2-C30 acylamino group, preferably, a C2-C20 acylamino group, more preferably, a C2-C10 acylamino group), an alkoxycarbonylamino group (for example, a C2-C30 alkoxycarbonylamino group, preferably, a C2-C20 alkoxycarbonylamino group, more preferably, a C2-C12 alkoxycarbonylamino group), an aryloxycarbonylamino group (for example, a C7-C30 aryloxycarbonylamino group, preferably, a C7-C20 aryloxycarbonylamino group, more preferably, a C7-C12 aryloxycarbonylamino group), a sulfonylamino group (for example, a C1-C30 sulfonylamino group, preferably, a C1-C20 sulfonylamino group, more preferably, a C1-C12 sulfonylamino group), a sulfamoyl group (for example, a C0-C30 sulfamoyl group, preferably, a C0-C20 sulfamoyl group, more preferably, a C0-C12 sulfamoyl group), a carbamoyl group (for example, a C1-C30 carbamoyl group, preferably, a C1-C20 carbamoyl group, more preferably, a C1-C12 carbamoyl group), an alkylthio group (for example, a C1-C30 alkylthio group, preferably, a C1-C20 alkylthio group, more preferably, a C1-C12 alkylthio group), an arylthio group (for example, a C6-C30 arylthio group, preferably, a C6-C20 arylthio group, more preferably, a C6-C12 arylthio group), a heterocyclicthio group (for example, a C1-C30 heterocyclicthio group, preferably, a C1-C20 heterocyclicthio group, more preferably, a C1-C12 heterocyclicthio group), a sulfonyl group (for example, a C1-C30 sulfonyl group, preferably, a C1-C20 sulfonyl group, more preferably, a C1-C12 sulfonyl group), a sulfynyl group (for example, a C1-C30 sulfynyl group, preferably, a C1-C20 sulfynyl group, more preferably, a C1-C12 sulfynyl group), an ureido group (for example, a C1-C30 ureido group, preferably, a C1-C20 ureido group, more preferably, a C1-C12 ureido group), a phosphoric acid amid group (for example, a C1-C30 phosphoric acid amid group, preferably, a C1-C20 phosphoric acid amid group, more preferably, a C1-C12 phosphoric acid amid group), a hydroxyl group, a mercapto group, a halogen atom, a cyano group, a sulfo group, a carboxyl group, a nitro group, a hydroxamine acid group, a sulfino group, a hydrazino group, an imino group, a heterocyclic group (for example, a C1-C30 heterocyclic group, preferably, a C1-C12 heterocyclic group), a silyl group (for example, a C3-C40 silyl group, preferably, a C3-C30 silyl group, more preferably, a C3-C24 silyl group), and a silyloxy group (for example, a C3-C40 silyloxy group, preferably, a C3-C30 silyloxy group, more preferably, a C3-C24 silyloxy group).

The cyclometalated transition metal complex represented by Formula 1 may be represented by Formula 5:

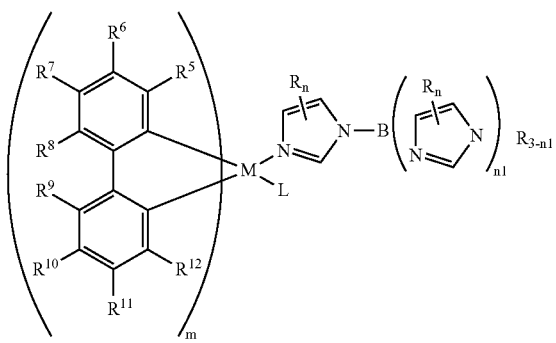

(5)

where M is a transition metal;

L is a neutral ligand;

m is 1 or 2;

$R^5$, $R^6$, $R^7$, $R^8$, $R^9$, $R^{10}$, $R^{11}$, $R^{12}$, R, and R' are each independently a substituent or a hydrogen atom where n is 1, 2 or 3; and n1 is 1, 2 or 3.

In Formulae 1 through 4, CY1 and CY2 may include an aromatic hydrocarbon ring such as a benzene ring or a naphthalene ring; an aromatic heterocycle, such as a pyridine ring, a pyrazine ring, a quinoline ring, a furane ring, or a thiophene ring; an aliphatic hydrocarbon ring such as a cyclohexen ring; an aliphatic heterocycle such as a pyrane ring; or the like.

That is, the cyclometalated ligand (CY1-CY2) may be represented by, but is not limited to, one of the following Formulae:

1-(i)

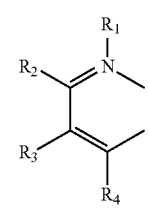

1-(ii)

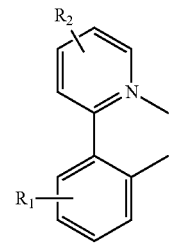

-continued
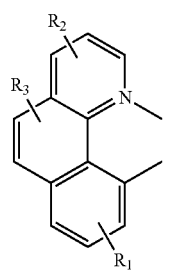
1-(iii)
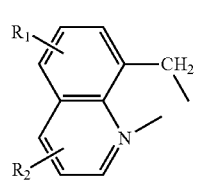
1-(iv)
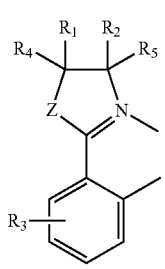
1-(v)
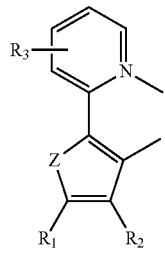
1-(vi)
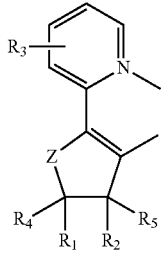
1-(vii)
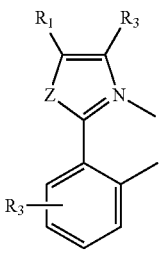
1-(viii)
-continued
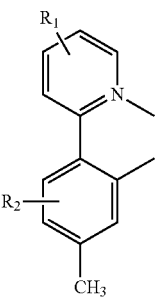
1-(ix)
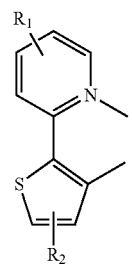
1-(x)
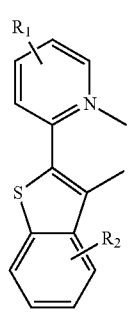
1-(xi)
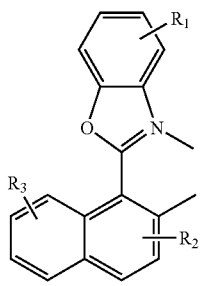
1-(xii)
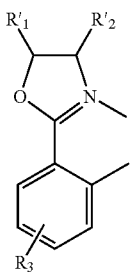
1-(xiii)

-continued
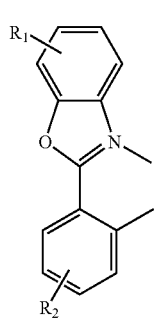
1-(xiv)
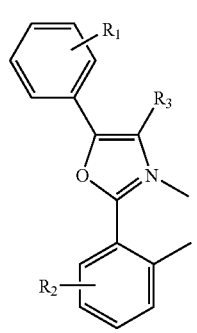
1-(xv)
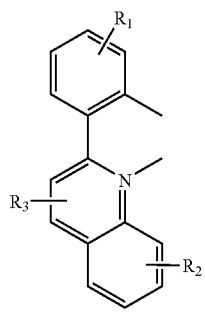
1-(xvi)
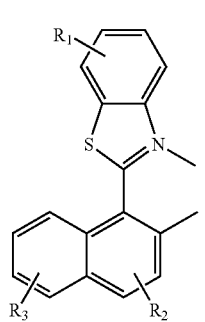
1-(xvii)
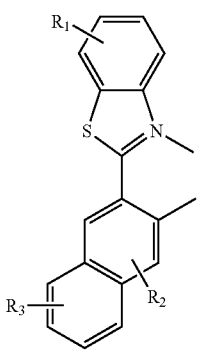
1-(xviii)
-continued
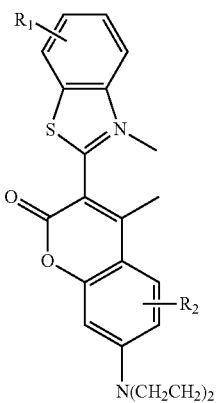
1-(xix)
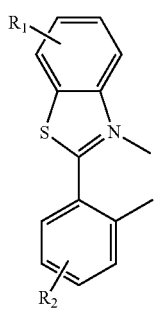
1-(xx)
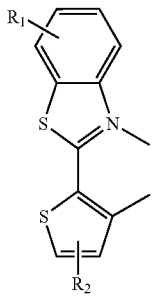
1-(xxi)
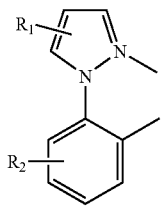
1-(xxii)
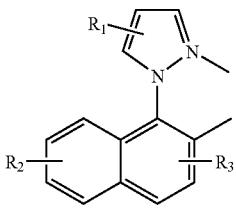
1-(xxiii)

—CN, —NO$_2$, —SO$_2$, —SOR, —SO$_2$R, —SO$_3$R, a C1-C20 alkyl group, or a C6-C20 aryl group where R is as defined above; and Z is S, O, or NR$_0$ where R$_0$ is a hydrogen or a C1-C20 alkyl group.

L, which is a neutral ligand in Formulae 1 through 5, may be represented by, but is not limited to, one of the following Formulae:

where R$_1$, R$_2$, R$_3$, R$_4$, and R$_5$, which are single-substituted groups or multi-substituted functional groups, are each independently a hydrogen atom, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), -continued

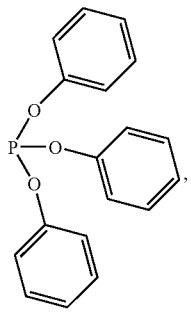
(1-(xxxviii))

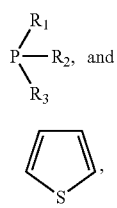
(1-(xxxix))

(1-(xxxx))

where R, $R_1$, $R_2$, and $R_3$ are each independently an alkyl group, an alkoxy group, an aryl group, an aryloxy group, or a heteroaryl group.

H in the neutral ligand can be substituted with an alkyl group, an alkoxy group, an aryl group, an aryloxy group, a heteroaryl group, a silyl group, a nitril group, a hydroxy group, or a halogen group.

M, which is a transition metal of Formulae 1 through 5, may be Ru, Rh, Os, Ir, Pt, or Au.

The cyclometalated transition metal complex represented by Formula 1 can be represented by, but is not limited to, one of Formulae 6 through 16:

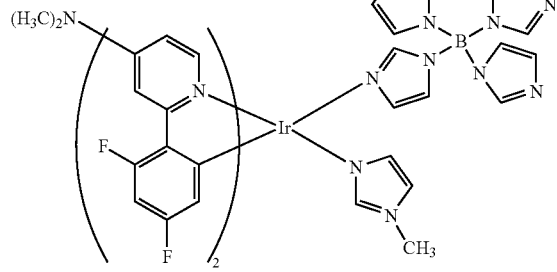
(6)

(7)

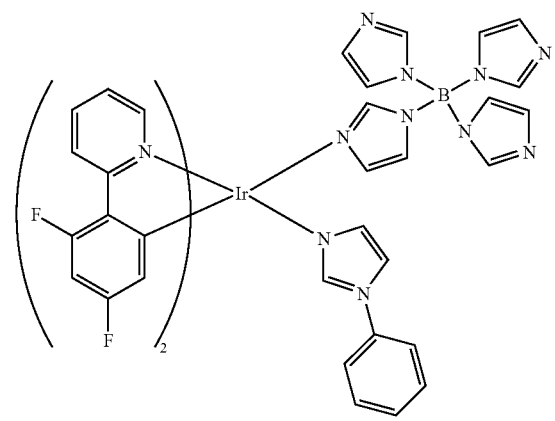
(8)

(9)

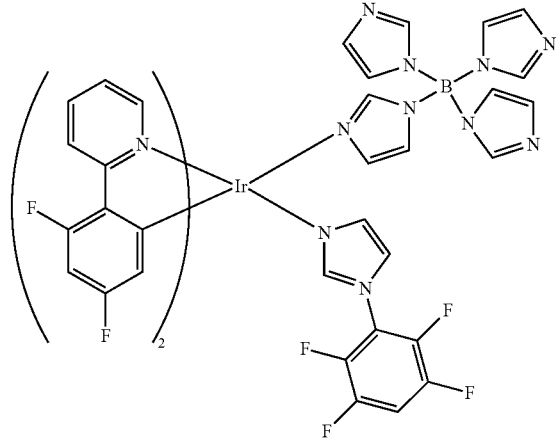
(10)

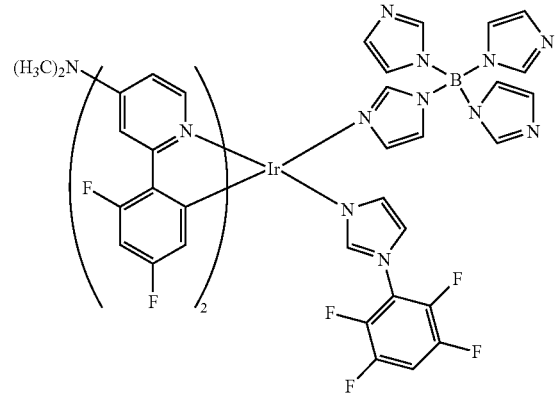
(11)

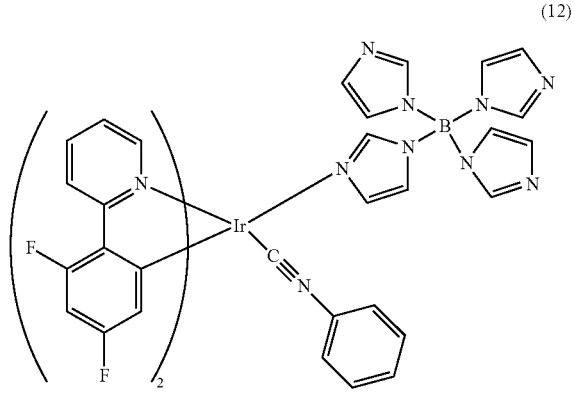

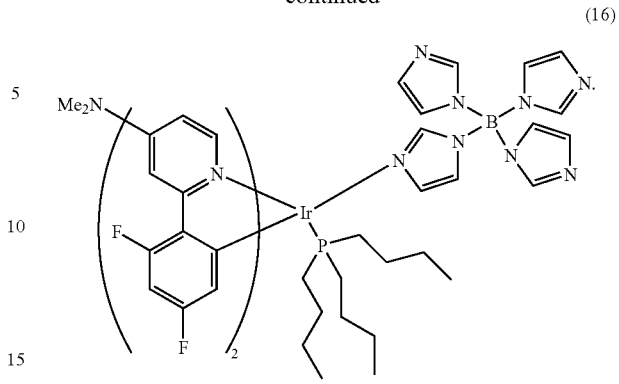

The cyclometalated transition metal complex may emit light with a wavelength of 400 nm of 650 nm.

The cyclometalated transition metal complex can be synthesized using a [Ir(C^N)₂ClL]₂ derivative, which is used as a starting material to provide a cyclometalated moiety, and a method disclosed by Watts Group (See F. O. Garces, R. J. Watts, Inorg. Chem. 1988, (35), 2450, which is incorporated herein by reference.)

Methods of synthesizing the cyclometalated transition metal complex will now be described.

Referring to Reaction Scheme 1, the [Ir(C^N)₂ClL]₂ derivative as a starting material and a boron compound are mixed with a solvent, such as dichloromethane or methanol, for 2 to 48 hours at 50° C., thus producing a cyclometalated transition metal complex containing a boron imidazole ligand represented by Formula 17.

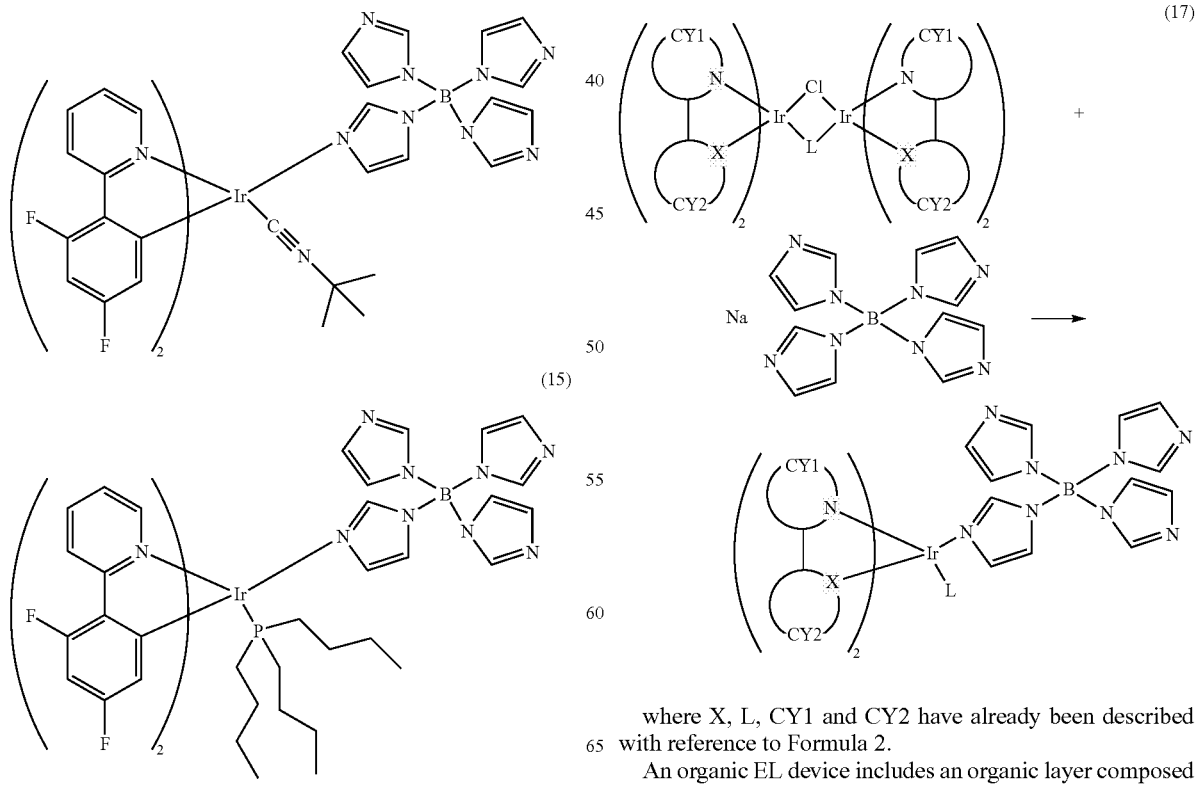

where X, L, CY1 and CY2 have already been described with reference to Formula 2.

An organic EL device includes an organic layer composed of the cyclometalated transition metal complex represented by Formula 1, in particular, an emission layer composed of the cyclometalated transition metal complex represented by Formula 1. The cyclometalated transition metal complex represented by Formula 1 is suitable as a phosphorescent dopant material for forming an emission layer and exhibits excellent blue emission characteristics.

When the cyclometalated transition metal complex represented by Formula 1 is used as the phosphorescent dopant, the organic layer may further include at least one host selected from at least one polymer host, a mixture host of a polymer and a low molecular weight molecule, a low molecular weight molecule host, and a non-emission polymer matrix. Any polymer host, any low molecular weight host, and any non-emission polymer matrix which are commonly used to manufacture an emission layer of an organic EL device can be used in the present embodiment. The polymer host may be, but is not limited to, poly(vinylcarbazole) (PVK) or polyfluorene. The low molecular weight host may be, but is not limited to, 4,4'-N,N'-dicarbazole-biphenyl (CBP), 4,4'-bis[9-(3,6-biphenylcarbazolyl)]-1,1'-biphenyl, 9,10-bis[(2',7'-t-butyl)-9', 9''-spirobifluorenyl anthracene, or terafluorene. The non-emission polymer matrix may be, but is not limited to, polymethylmethacrylate, or polystyrene.

The amount of the cyclometalated transition metal complex represented by Formula 1 may be in the range of 1 to 30 parts by weight based on 100 parts by weight of the total amount of an emission layer forming material. An emission layer may be formed with the cyclometalated transition metal complex by vacuum deposition, sputtering, printing, coating, ink-jet printing, an electron beam, or other methods.

The cyclometalated transition metal complex represented by Formula 1 can emit white light when used with a green emissive material or a red emissive material.

The thickness of the organic layer may be in the range of 30 to 100 nm. In this case, the term 'organic layer' indicates a layer composed of an organic material interposed between a pair of electrodes of an organic EL device. For example, the organic layer can be the emission layer, the electron transport layer, the hole transport layer, or the like. The organic EL device may have a structure such as anode/emission layer/cathode, anode/buffer layer/emission layer/cathode, anode/hole transport layer/emission layer/cathode, anode/buffer layer/hole transport layer/emission layer/cathode, anode/buffer layer/hole transport layer/emission layer/electron transport layer/cathode, anode/buffer layer/hole transport layer/emission layer/hole blocking layer/cathode, or the like. However, the structure of the organic EL device is not limited thereto.

The buffer layer may be composed of a commonly used material. For example, a material for forming the buffer layer may be, but is not limited to, copper phthalocyanine, polythiophene, polyaniline, polyacetylene, polypyrrole, polyphenylene vinylene, or derivatives thereof.

A material for forming the hole transport layer may be a commonly used material. For example, the material for forming the hole transport layer may be, but is not limited to, polytriphenylamine.

A material for forming the electron transport layer may be a commonly used material. For example, the material for forming the electron transport layer may be, but is not limited to, polyoxadiazole.

A material for forming the hole blocking layer may be a commonly used material. For example, the material for forming the hole blocking layer may be, but is not limited to, LiF, $BaF_2$, or $MgF_2$.

The organic EL device according to an embodiment of the present invention can be manufactured using conventional emissive materials and conventional methods.

The cyclometalated transition metal complex may emit light with a wavelength of 400 nm to 650 nm. An emission diode using such a transition metal complex can be used in light source illumination for a full-color display, a backlight, outdoor screens, optical communication, and interior decoration.

The present invention will now be described in further detail with reference to the following examples. These examples are for illustrative purposes only and are not intended to limit the scope of the present invention.

REFERENCE EXAMPLE 1

Synthesis of $F_2$ppy Dimer (18)

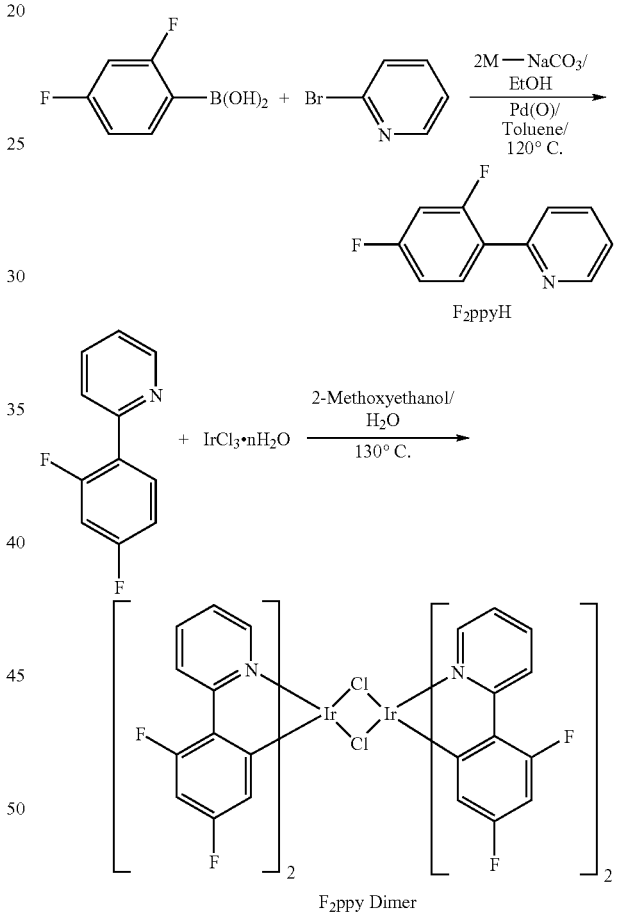

A 2M sodium carbonate solution that was prepared by mixing 19.85 g (125 mmol) of 2-bromopyridine, 25.00 g (158 mmol) of 2,4-difluorophenyl boronic acid, 100 ml of toluene, 48 ml of ethanol, and 95 ml of water was added to a 500 ml branched flask and stirred in a nitrogen atmosphere at room temperature. Subsequently, 4.53 g (3.92 mmol) of tetrakis(triphenylphosphine)paladium(0) was added to the reaction mixture and refluxed in the nitrogen atmosphere without the presence of light for 15 hours.

After the reaction was completed, the resulting reaction mixture was controlled to room temperature and extracted using ethylacetate and water. The extract was separated using column chromatography (toluene:hexane=10:1), thus obtaining a light brown liquid (F$_2$ppyH).

$^1$H-NMR(CD$_2$Cl$_2$,ppm): 8.69[d, 1H], 8.03[m, 1H], 7.70 [m, 2H], 7.27[m, 1H], 7.00[m, 2H]

A yellow powder F$_2$ppyIr dimer of Formula 18 was prepared using the 2-(4,6-difluorophenylpyridine) monomer and IrCl$_3$·nH$_2$O. In this case, the synthesis method disclosed in J. Am. Chem. Soc., 1984, 106, 6647-6653, which is incorporated herein by reference, was used.

$^1$H-NMR(CD$_2$Cl$_2$,ppm): 9.1[d, 4H], 8.3[d, 4H], 7.9[t, 4H], 6.9[m, 4H], 6.5[m, 4H], 5.3[d, 4H]

REFERENCE EXAMPLE 2

Synthesis of MeOF$_2$ppy Dimer

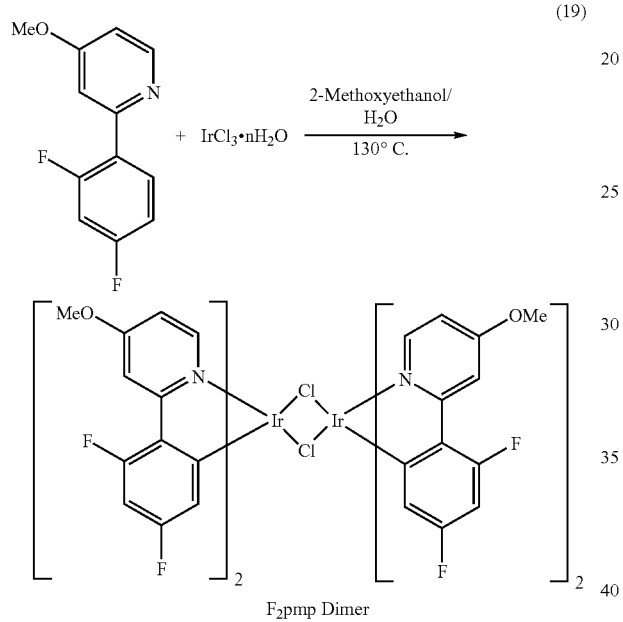

F$_2$pmp Dimer

A MeOF$_2$ppy dimer represented by Formula 19 was synthesized in the same manner as in Reference Example 1, except that 2-bromo-4-methoxypyridine was used instead of 2-bromopyridine.

REFERENCE EXAMPLE 3

Synthesis of DMAF$_2$ppy Dimer

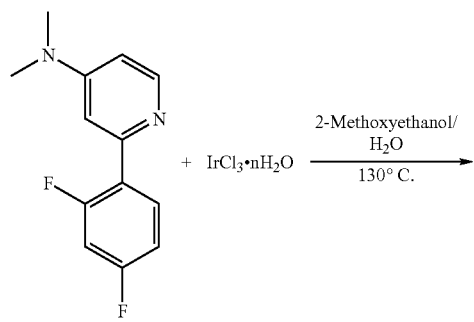

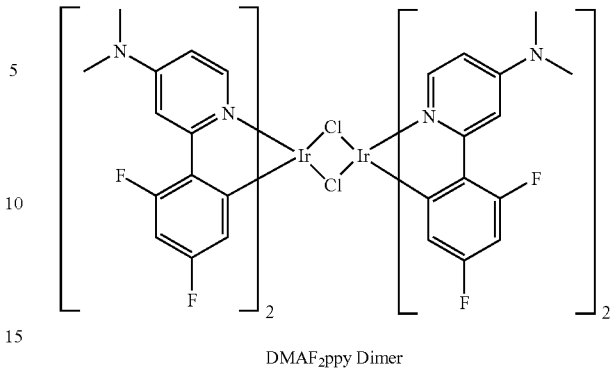

DMAF$_2$ppy Dimer

A DMAF$_2$ppy dimer of Formula 20 was synthesized in the same manner as in Reference Example 1, except that 25.26 g (1.25×10$^4$ mmol) of 2-bromo-4-dimethylaminopyridine was used instead of 2-bromopyridine.

$^1$H-NMR(CD$_2$Cl$_2$,ppm): 8.7 (d, 4H), 7.5 (t, 4H), 6.3 (m, 4H), 6.1 (m, 4H) 5.4 (d, 4H), 3.2 (s, 24H)

Example 1

Synthesis of Compound Represented by Formula 7 ((MeOF$_2$ppy)$_2$IrMe-imz Bimz$_4$)

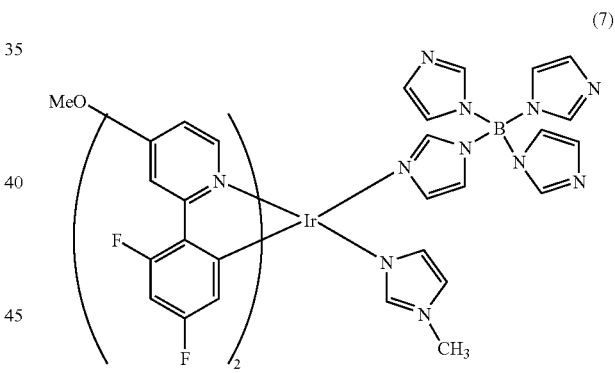

Operation 1. Synthesis of MeOF$_2$ppyIrMe-imz Cl mmol of the MeOF$_2$ppy dimer of Formula 19 and 0.25 mmol of an N-methyl imidazole were stirred in 20 ml of CHCl$_3$ at 40° C. for 6 hours. The solvent was vaporized under reduced pressure, and the resulting yellow green powder was subjected to a silica column using a mixture of CH$_2$Cl$_2$ and acetone in a ratio of 10:0.5 as an eluent. After the solvent was vaporized, a green powder was obtained. MeOF$_2$ppyIrMe-imz Cl was identified using $^1$H NMR and Mass spectra.

Operation 2. Synthesis of (MeOF$_2$ppy)$_2$IrMe-imz Bimz$_4$ 0.5 mmol of NaBimz$_4$ and 10 ml of methanol were added to 0.1 mmol of MeOF$_2$ppyIrMe-imz Cl dissolved in 10 ml of chloroform, and then stirred at 50° C. for 4 to 6 hours. The solvent was removed by vaporization under reduced pressure, and the result was treated with 20 ml of CH$_2$Cl$_2$ and filtered. The filtrate was under reduced pressure so that the CH$_2$Cl$_2$ could be removed by vaporization. As a result, yellow green powder (Yield: 65%) was attained. (MeOF$_2$ppy)$_2$IrMe-imz Bimz$_4$ was identified using $^1$H NMR and Mass spectra.

Example 2

Synthesis of Compound Represented by Formula 8 ((DMAF$_2$ppy)$_2$IrMe-imz Bimz$_4$)

(8)

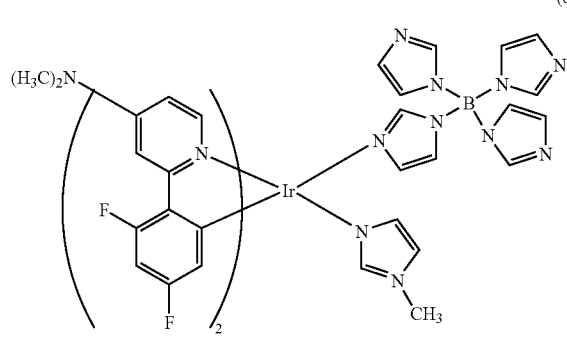

(DMAF$_2$ppy)$_2$IrMe-imz Bimz$_4$ was produced from a corresponding dimer in the same manner as in Example 1 (Yield: 65%.) The (DMAF$_2$ppy)$_2$IrMe-imz Bimz$_4$ was identified using $^1$H NMR and Mass spectra.

Example 3

Synthesis of Compound Represented by Formula 9 ((F$_2$ppy)$_2$IrPh-imz Bimz$_4$)

(9)

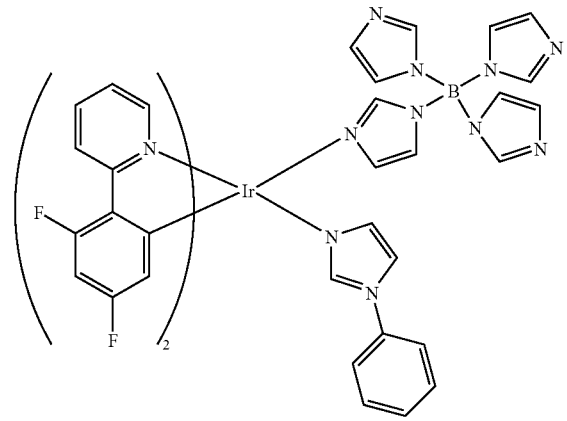

(F$_2$ppy)$_2$IrPh-imz Bimz$_4$ was produced from a corresponding dimer in the same manner as in Example 1 (Yield: 65%.) (F$_2$ppy)$_2$IrPh-imz Bimz$_4$ was identified using $^1$H NMR and Mass spectra.

Example 4

Synthesis of Compound Represented by Formula 13 ((F$_2$ppy)$_2$IrBenz-iso-CN Bimz$_4$)

(13)

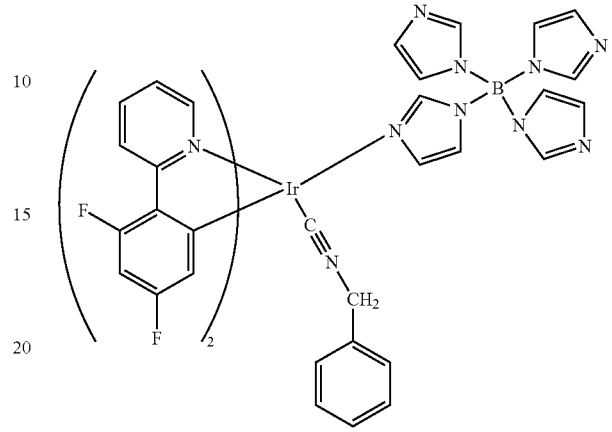

(1) Synthesis of F$_2$ppyIrBenz-iso-CN Cl 0.1 mmol of the F$_2$ppy dimer of Formula 18 and 0.25 mmol of benzylisocyanid (benz-iso-CN) were stirred in 20 ml of CHCl$_3$ at room temperature for 24 hours. The solvent was vaporized under reduced pressure, and the resulting yellow powder was subjected to a silica column using a mixture of CH$_2$Cl$_2$ and acetone in a ratio of 10:0.5 as an eluent. After the solvent was vaporized, a yellow powder was obtained. F$_2$ppyIrBenz-iso-CN Cl was identified using $^1$H NMR and Mass spectra.

(2) Synthesis of (F$_2$ppy)$_2$IrBenz-iso-CN Bimz$_4$ 0.5 mmol of NaBimz$_4$ and 10 ml of methanol were added to 0.1 mmol of F$_2$ppyIrBenz-iso-CN Cl dissolved in 10 ml of chloroform, and then stirred at 50° C. for 4 to 6 hours. The solvent was removed by vaporization under reduced pressure, and the result was treated with 20 ml of CH$_2$Cl$_2$ and filtered. The filtrate was under reduced pressure so that the CH$_2$Cl$_2$ could be removed by vaporization. As a result, a yellow powder (Yield: 50%) was attained. (F$_2$ppy)$_2$IrBenz-iso-CN BimZ$_4$ was identified using $^1$H NMR and Mass spectra.

Example 5

Synthesis of Compound Represented by Formula 15 ((F$_2$ppy)$_2$IrP(n-bu)$_3$ Bimz$_4$)

(15)

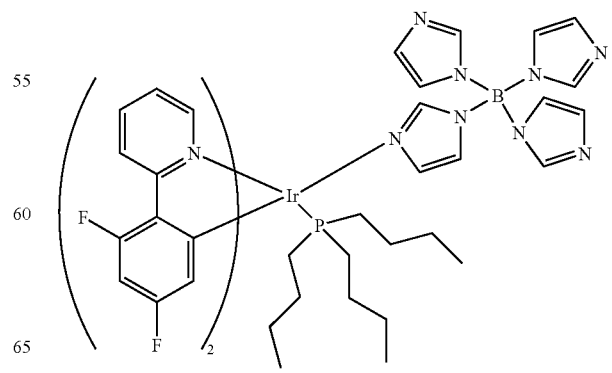

(1) Synthesis of $F_2ppyIrP(n-bu)_3$ Cl mmol of the $F_2ppy$ dimer of Formula 18 and 0.25 mmol of tri-n-butyl were stirred in 20 ml of $CHCl_3$ at room temperature for 24 hours. The solvent was vaporized under reduced pressure, and the resulting yellow powder was subjected to a silica column using a mixture of $CH_2Cl_2$ and acetone in a ratio of 10:1 as an eluent. After the solvent was vaporized, a yellow powder was obtained. $F_2ppyIrP(n-bu)_3$ Cl was identified using $^1$H NMR and Mass spectra.

(2) Synthesis of $(F_2ppy)_2IrP(n-bu)_3$ $Bimz_4$ 0.5 mmol of $NaBimz_4$ and 10 ml of methanol were added to 0.1 mmol of $F_2ppyIrP(n-bu)_3Cl$ dissolved in 10 ml of chloroform, and then stirred at 50° C. for 4 to 6 hours. The solvent was removed by vaporization under reduced pressure, and the result was treated with 20 ml of $CH_2Cl_2$ and filtered. The filtrate was under reduced pressure so that the $CH_2Cl_2$ could be removed by vaporization. As a result, a yellow powder (Yield: 60%) was attained. $(F_2ppy)_2IrP(n-bu)_3Bimz_4$ was identified using $^1$H NMR and Mass spectra.

The products obtained according to Examples 1 through 5 were dissolved in methylene chloride to prepare $10^{-4}$ M solutions, and luminance characteristics of these solutions were measured.

Figure 5:
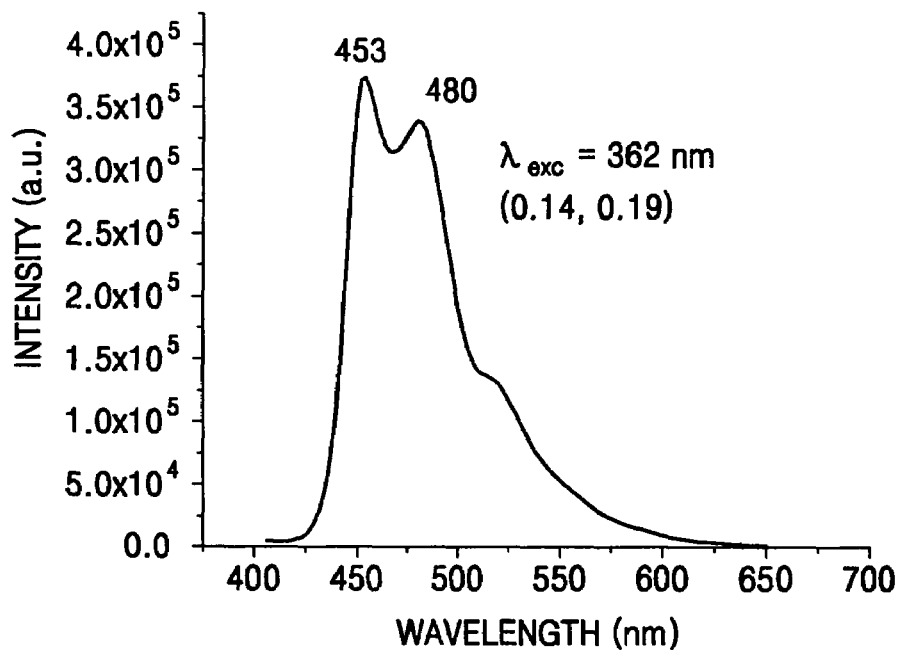
FIG. 5 illustrates a photoluminescence (PL) spectrum of a compound according to Example 1.
Figure 6:
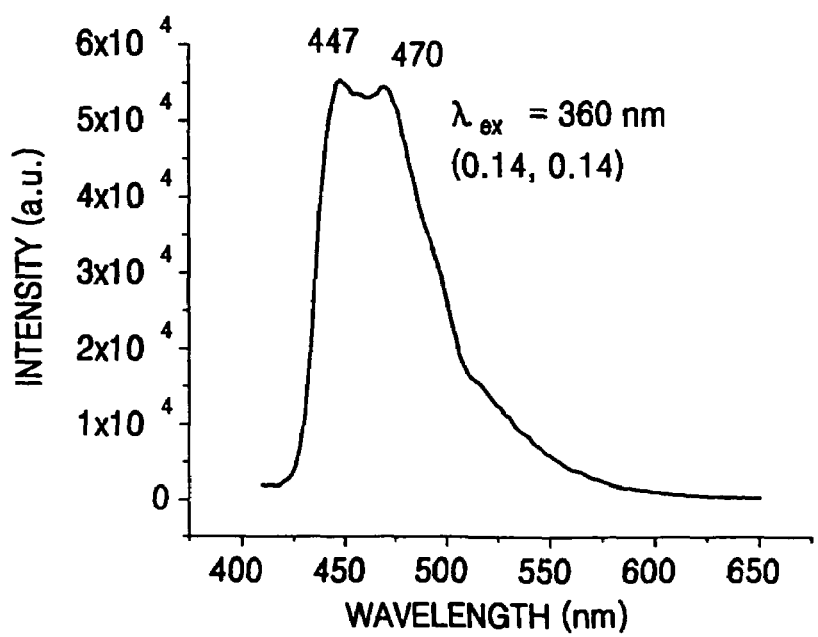
FIG. 6 illustrates a PL spectrum of a compound according to Example 2.
Figure 7:
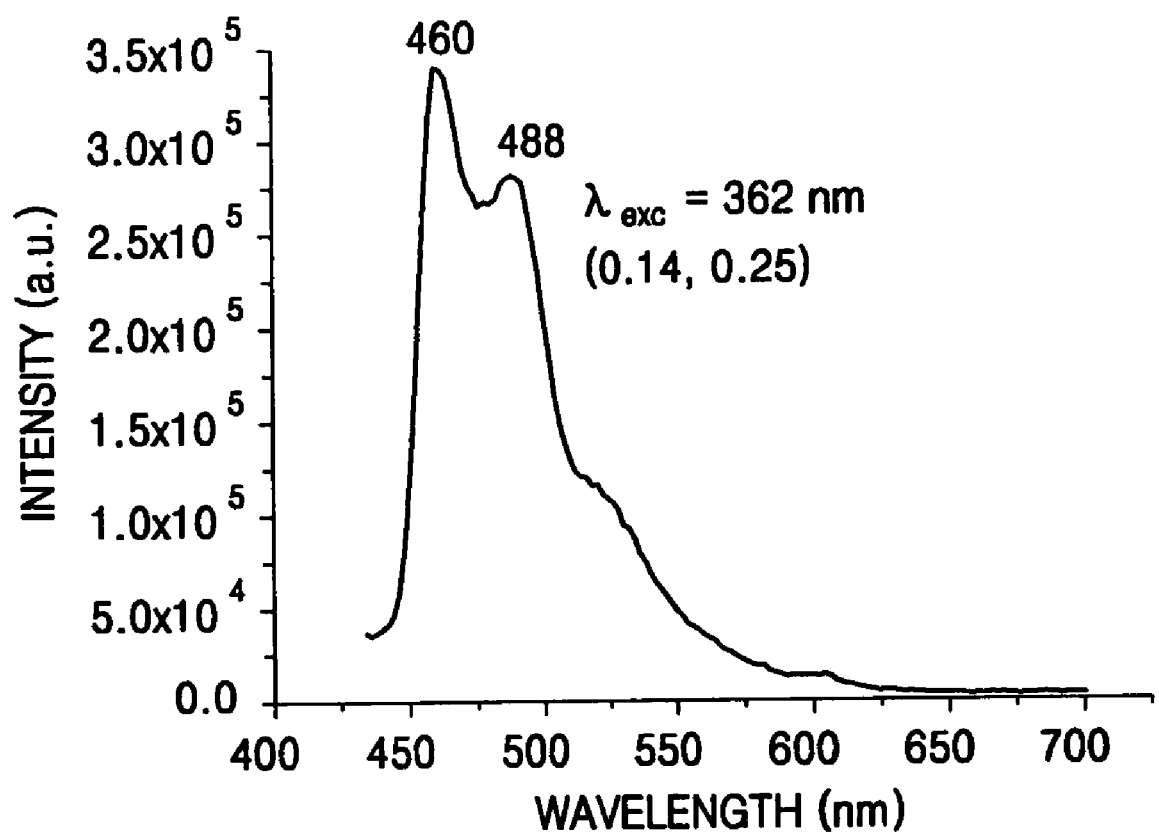
FIG. 7 illustrates a PL spectrum of a compound according to Example 3.

The luminance characteristics and color coordinates (CIE) of these products are shown in Table 1, and FIGS. 5 through 7 illustrate PL spectra of the products of Examples 1 to 3, respectively. FIGS. 1 through 4 illustrate mass spectrums of compound according to Examples 1, 3, 4 and 5, respectively.

TABLE 1

| Compound | $\lambda_{em}$ nmP(film) | CIE(x,y) |
|---|---|---|
| 6 | 460, 490 | 0.14, 0.23 |
| 7 | 453, 480 | 0.14, 0.19 |
| 8 | 447, 470 | 0.14, 0.14 |
| 9 | 460, 488 | 0.14, 0.25 |
| 10 | 462, 488 | 0.14, 0.20 |
| 11 | 450, 464 | 0.15, 0.15 |
| 12 | 450, 477 | 0.15, 0.20 |
| 13 | 452, 479 | 0.15, 0.20 |
| 14 | 450, 479 | 0.14, 0.20 |
| 15 | 456, 482 | 0.14, 0.20 |
| 16 | 441, 461 | 0.15, 0.12 |

Referring to Table 1, dopants containing a boron imidazole complex compound exhibited excellent phosphorescent characteristics. In particular, the introduction of the substituent resulted in a strong electronic effect, and thus, it was confirmed that the dopant is suitable as a blue phosphorescent material emitting light with a wavelength of 440 nm to 470 nm.

Figure 8:
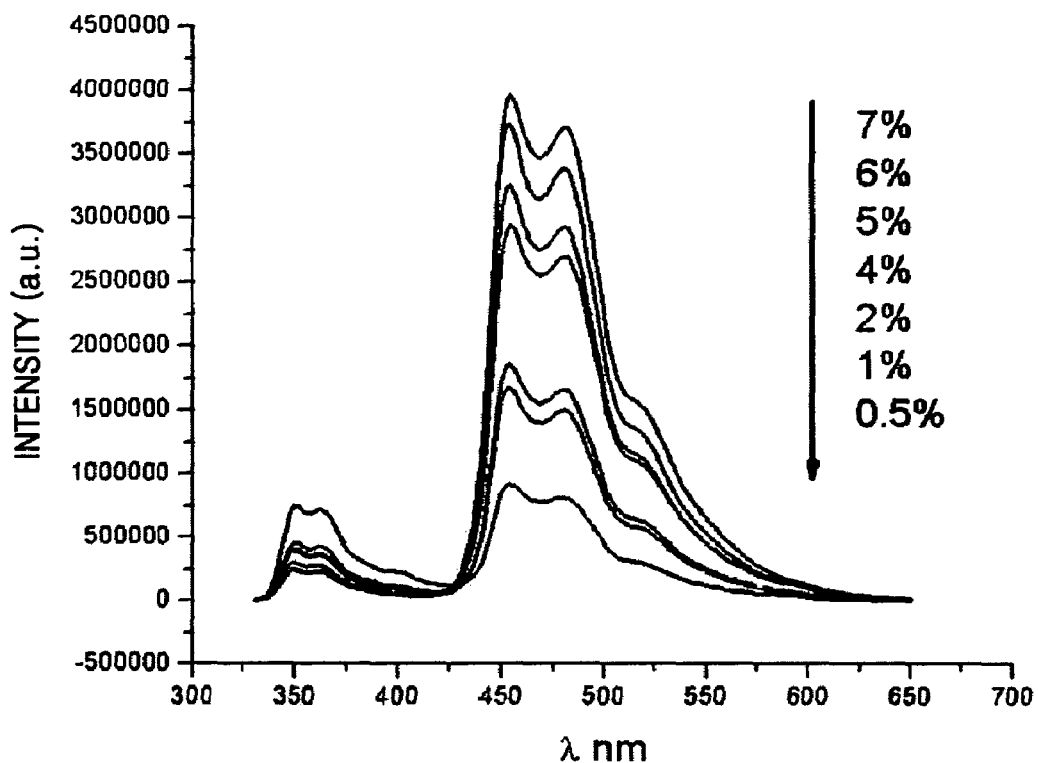
FIGS. 8 and 9 illustrate energy transition when the concentration of the compound according to Example 1 varies.
Figure 9:
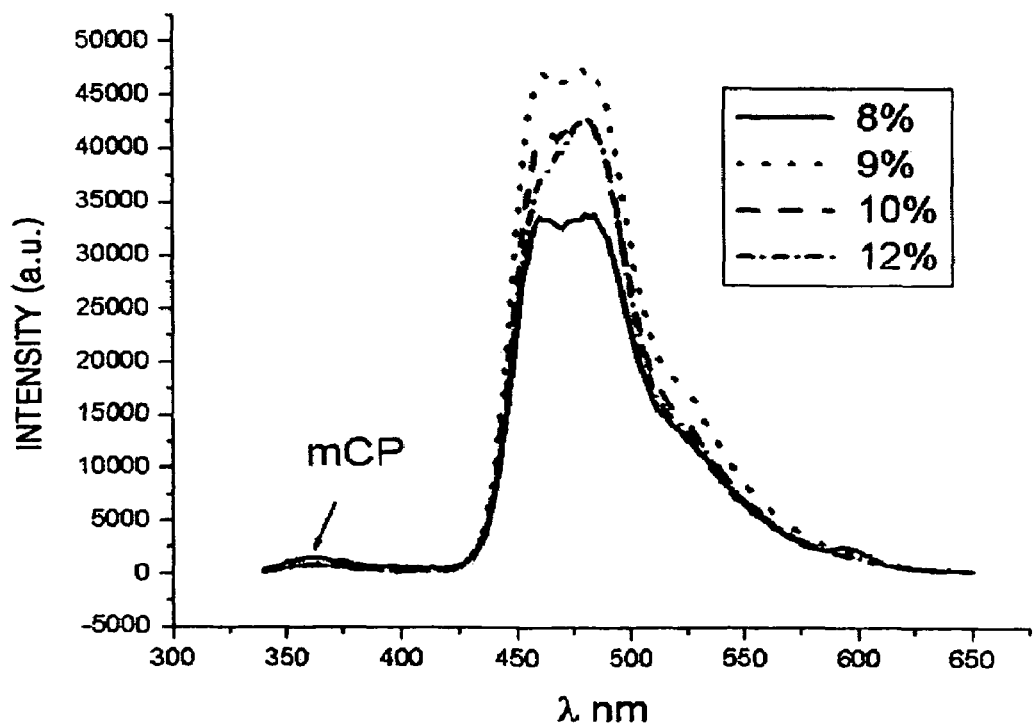
Figure 10:
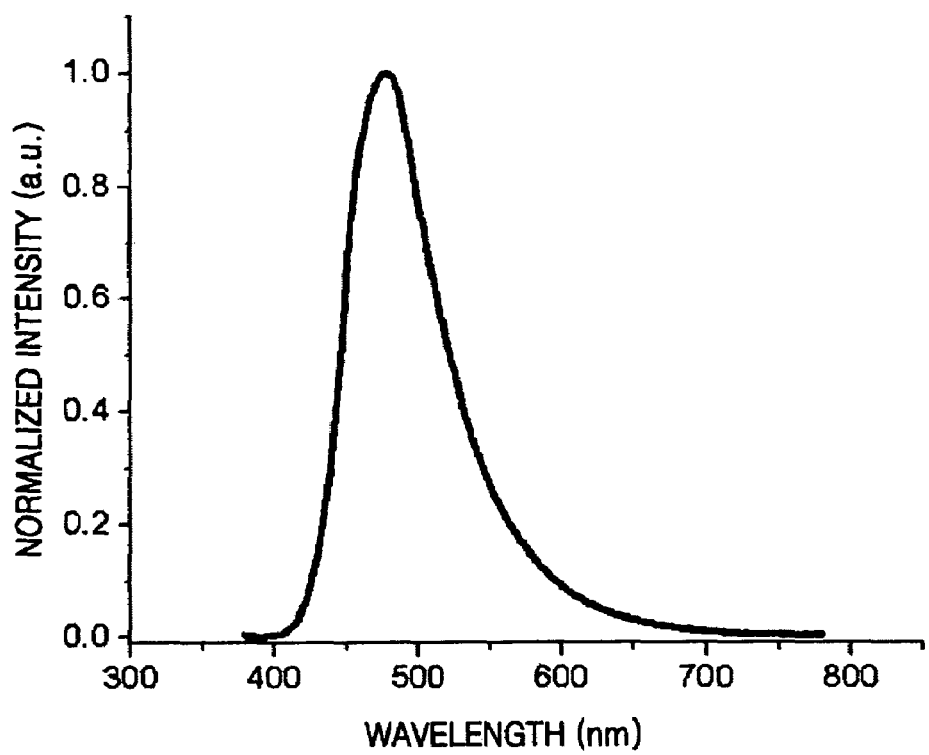
FIG. 10 illustrates an electroluminance (EL) spectrum of an organic EL device according to Example 7.

FIGS. 8 and 9 illustrate the energy transition of the compound represented by Formula 7 according to Example 1 when the concentration of the compound varies. In this case, mCP was used as a host material, and the compound represented by Formula 7 $[(MeOF_2ppy)_2IrMe-imz_4]$ was used as a dopant material. Referring to FIGS. 8 and 9, when the concentration of the dopant was increased, the intensity of mCP decreased and the intensity of the dopant increased. Referring to FIG. 9, when the concentration of the dopant was 10% or greater, the intensity of the dopant decreased.

Manufacture of Organic EL Device

Example 6

Figure 13:
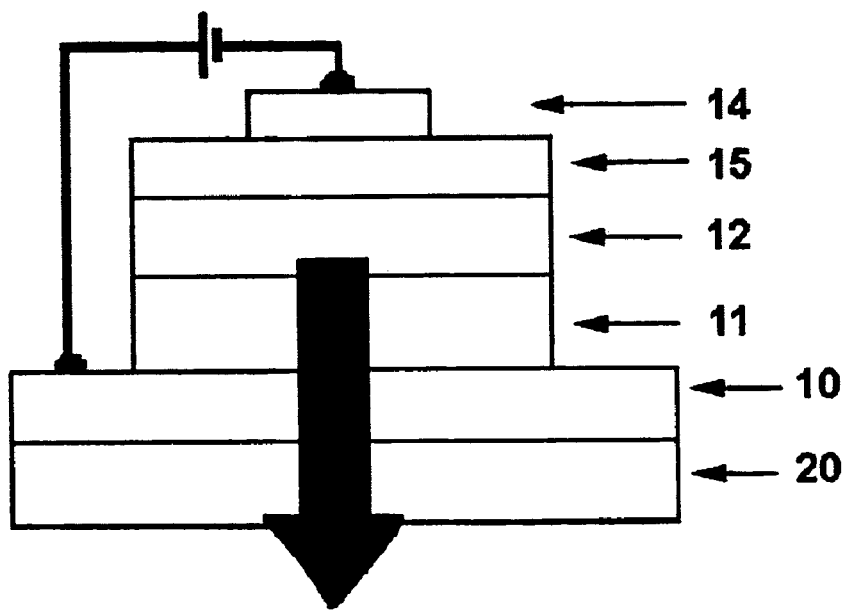
FIG. 13 is a schematic sectional view of the organic EL devices according to Examples 6 through 10.

Referring to FIG. 13, an indium-tin oxide (ITO)-coated transparent electrode substrate 20 was washed, and a pattern was formed in the ITO using a photoresist resin and an etchant, thus forming an ITO electrode pattern 10. The ITO electrode pattern was washed. PEDOT (poly(3,4-ethylene-dioxythiophene))[Al 4083] was coated on the washed ITO electrode pattern to a thickness of about 50 nm and baked at 120° C. for about 5 minutes to form a hole injection layer 11.

An emission layer forming composition, which was prepared by mixing 29 mg of mCP, 2.5 mg of $(F_2ppy)_2IrPh-imz$ $Bimz_4$ (represented by Formula 9), and 3.3 g of a polystyrene solution prepared by dissolving 53.1 g of polystyrene (PS) in 17.4 g of toluene was spin coated on the hole injection layer 11 and baked at 100° C. for 1 hour. The result was placed in a vacuum oven to completely remove the solvent, thus forming an emission layer 12 with a thickness of 40 nm [PS 24 wt %, mCP 70 wt %, $(F_2ppy)_2IrPh-imz$ $Bimz_4$ 6 wt %].

Then, Balq (aluminum(III)bis(2-methyl-8-quinolinato)$_4$-phenylphenolate) was vacuum deposited on the polymer emission layer 12 using a vacuum deposition device under a pressure of $4\times10^{-6}$ torr or less, thus forming an electron transport layer 15 with a thickness of 40 nm. LiF was vacuum deposited on the electron transport layer at a speed of 0.1 Å/sec to form an electron injection layer with a thickness of 10 nm.

Subsequently, Al was deposited on the electron transport layer 15 at a speed of 10 Å/sec to form a cathode 14 with a thickness of 200 nm, and encapsulated using a metal can in a glove box filled with BaO powder under a dry nitrogen gas atmosphere, thus completely manufacturing the organic EL device.

The EL device had a multi-layer structure and its schematic view is illustrated in FIG. 13. In this case, the emission area was 9 mm$^2$.

Example 7

An EL device was manufactured in the same manner as in Example 6 except that the amount of $(MeOF_2ppy)_2IrMe-imz_4$ (represented by Formula 7) was 6 wt %.

Example 8

An EL device was manufactured in the same manner as in Example 6 except that the amount of $(MeOF_2ppy)_2IrMe-imz$ $Bimz_4$ (represented by Formula 7) was 8 wt %.

Example 9

An EL device was manufactured in the same manner as in Example 6 except that the amount of $(MeOF_2ppy)_2IrMe-imz$ $Bimz_4$ (represented by Formula 7) was 10 wt %.

Example 10

An EL device was manufactured in the same manner as in Example 6 except that the amount of $(F_2ppy)_2IrP(n-bu)_3$ $Bimz_4$ (represented by Formula 15) was 10 wt %.

Figure 11:
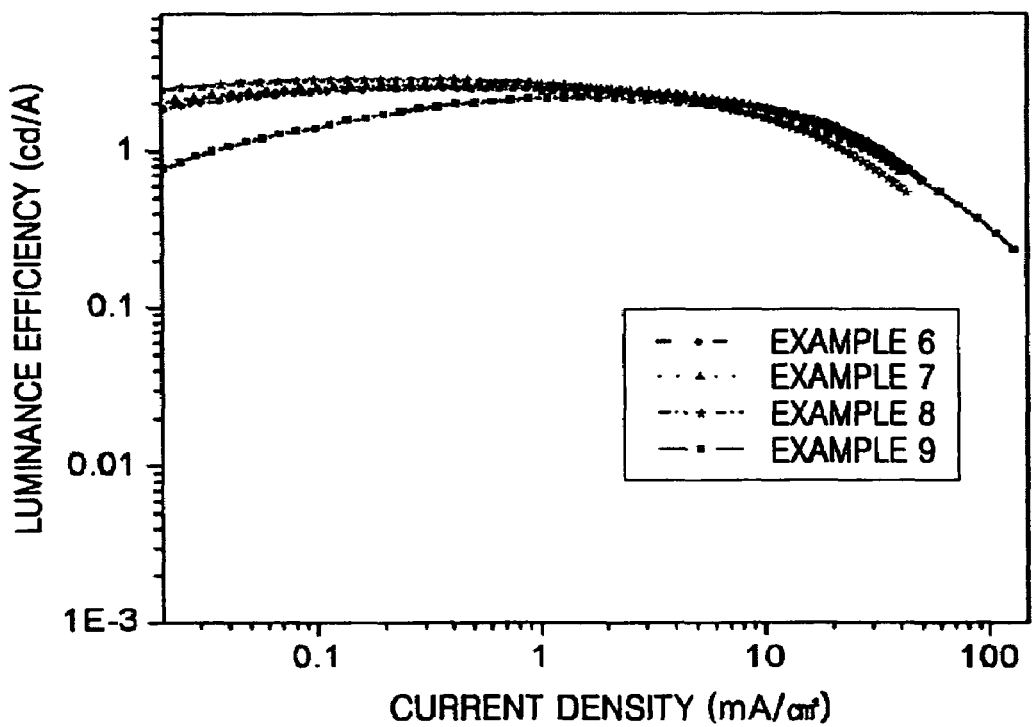
FIG. 11 is a graph of luminance efficiency with respect to current density of each organic EL device according to Examples 6 through 9.
Figure 12:
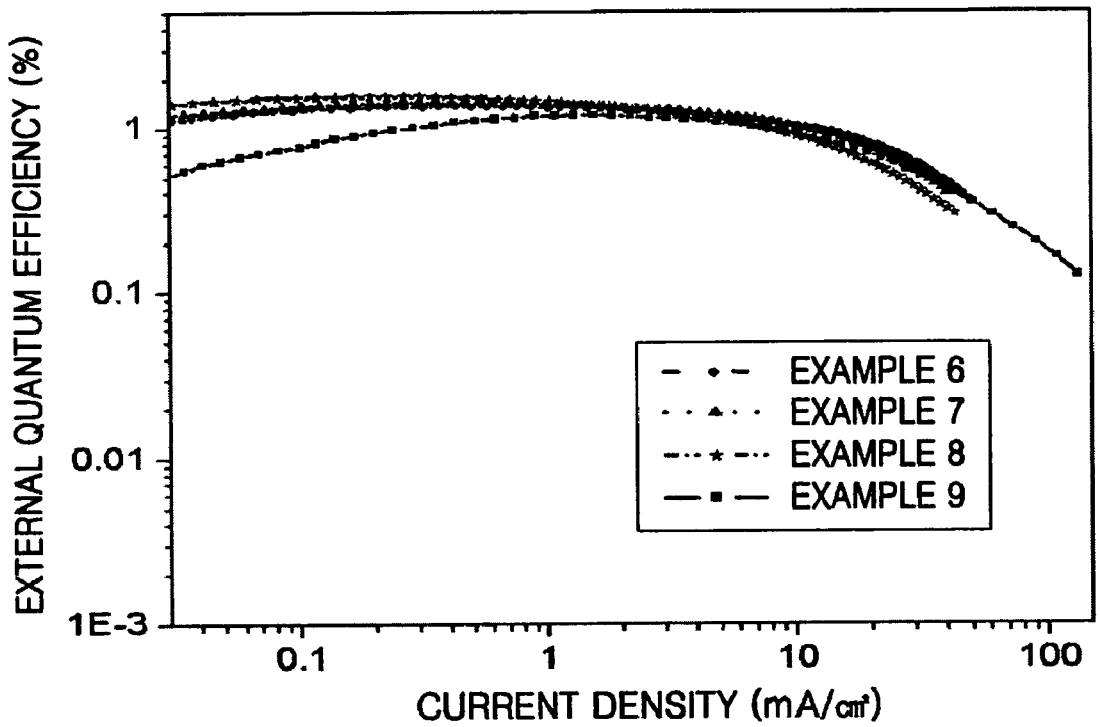
FIG. 12 is a graph of external quantum efficiency with respect to current density of each of the organic EL devices according to Examples 6 through 9.

Luminance efficiency with respect to current density and external quantum efficiency with respect to current density of each of the organic EL devices according to Examples 6 through 9 are shown in FIGS. 11 and 12.

Properties of the EL devices of Examples 6, 9, and 10 including maximum emission wavelength, color coordinate, luminance, and turn-on voltage are shown in Table 2.

TABLE 2

| Dopant | $\lambda_{max}$ nm EL | CIE EL | $\eta_{ex}$ (%) | $\eta_L$ (Cd/A) | Turn on V |
|---|---|---|---|---|---|
| Example 6 (Compound represented by Formula 9) | 465, 490 | 0.18, 0.32 | 1.21 | 2.2 | 8.4 |
| Example 9 (Compound represented by Formula 7) | 475 | 0.18, 0.28 | 1.56 | 2.85 | 7.2 |
| Example 10 (Compound represented by Formula 15) | 460, 480 | 0.18, 0.27 | 0.47 | 0.8 | 6.7 |

As described above, a dopant containing a boron imidazole complex ligand has excellent phosphorescent characteristics and is suitable for blue emission. In addition, by introducing various main ligands, full-color light including red, green, and blue can be realized.

A cyclometalated transition metal complex according to the present invention can effectively emit light ranging from a blue wavelength to a red wavelength through a triplet MLCT. The cyclometalated transition metal complex is suitable for an organic layer of an organic EL device, and very efficiently emits a phosphorescent light with a wave length of 400 nm to 650 nm. In addition, when the cyclometalated transition metal complex is used with a green emissive material or a red emissive material, a white light can be emitted.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A transition metal complex represented by Formula 1:

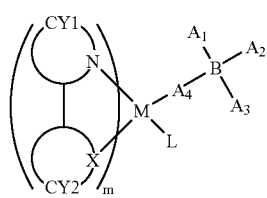

(1)

where M is a transition metal;
X is one of N and C;
L is a neutral ligand;
CY1 and CY2 are each independently an aromatic or aliphatic ring system, and CY1 contains a nitrogen atom that is bonded to M, and CY2 contains X that is bonded to M;
m is 1 or 2; and
$A_1, A_2, A_3$, and $A_4$ are each independently imidazole, pyrazole, a derivative of the imidazole, or a derivative of pyrazole.

2. The transition metal complex of claim 1, wherein the compound represented by Formula 1 is represented by one of Formulae 2 and 3:

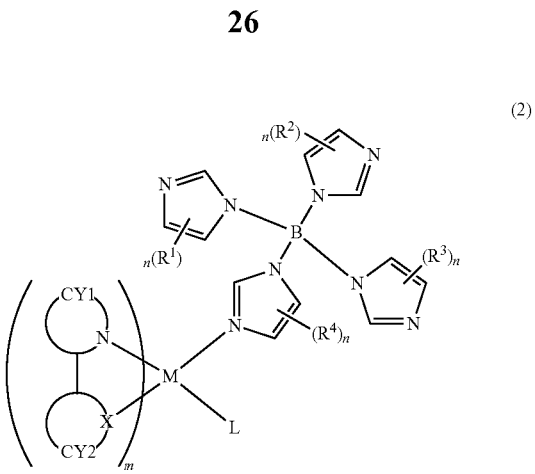

(2)

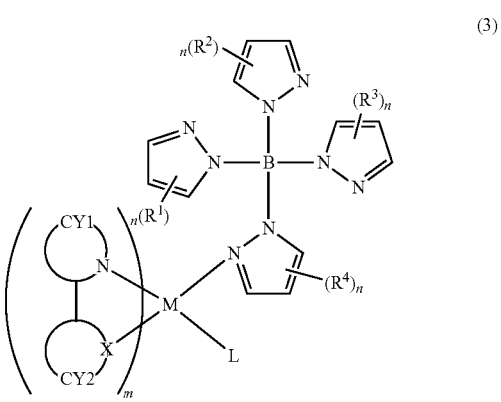

(3)

where M is a transition metal;
X is one of N and C;
L is a neutral ligand;
CY1 and CY2 are each independently an aromatic or aliphatic ring system;
m is 1 or 2;
$R^1$, $R^2$, $R^3$, and $R^4$ are each independently a substituent or H; and
n is 1, 2, or 3.

3. The transition metal complex of claim 1, wherein $A_1$, $A_2$, $A_3$, and $A_4$ are each independently substituted with one substituent selected from the group consisting of a hydrogen atom, an alkyl group, an alkenyl group, an alkynyl group, an aryl group, an amino group, an alkoxy group, an aryloxy group, a heterocyclicoxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclicthio group, a sulfonyl group, a sulfynyl group, an ureido group, a phosphoric acid amid group, a hydroxyl group, a mercapto group, a halogen atom, a cyano group, a sulfo group, a carboxyl group, a nitro group, a hydroxamine acid group, a sulfino group, a hydrazino group, an imino group, a heterocyclic group a silyl group, and a silyloxy group.

4. The transition metal complex of claim 1, wherein the compound represented by Formula 1 is represented by Formula 5:

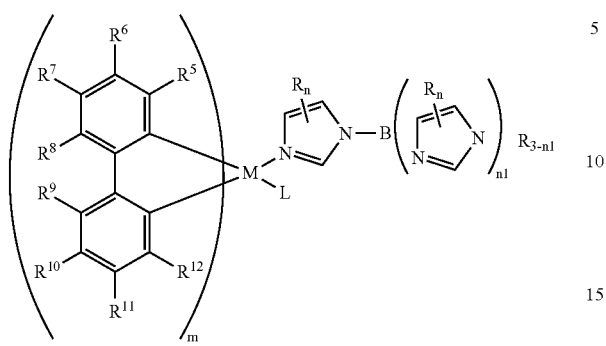

(5)

where M is a transition metal;
L is a neutral ligand;
m is 1 or 2;
$R^5$, $R^6$, $R^7$, $R^8$, $R^9$, $R^{10}$, $R^{11}$, $R^{12}$, R, and R' are each independently a substituent or a hydrogen atom where n is 1, 2, or 3; and
n1 is 3.

5. The transition metal complex of claim 1, wherein M is Ru, Rh, Os, Ir, Pt, Or Au.

6. The transition metal complex of claim 1, wherein the compound represented by Formula 1 is represented by one of Formulae 6 through 16:

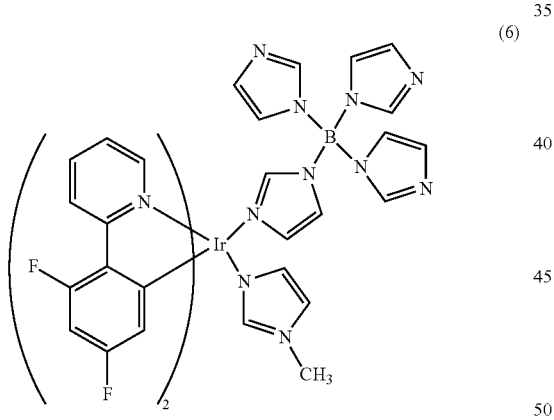

(6)

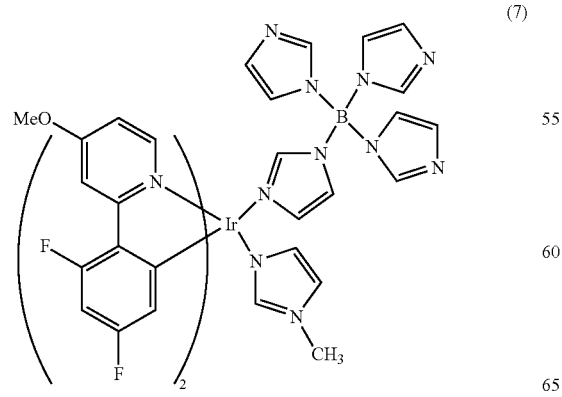

(7)

-continued

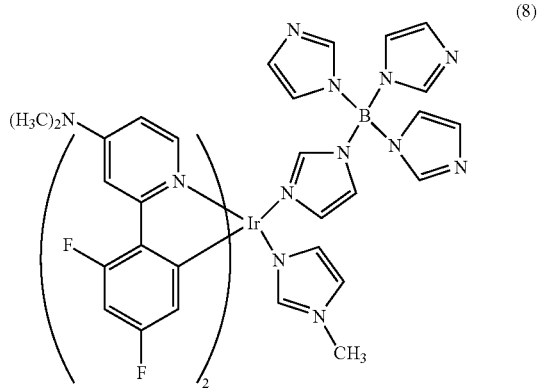

(8)

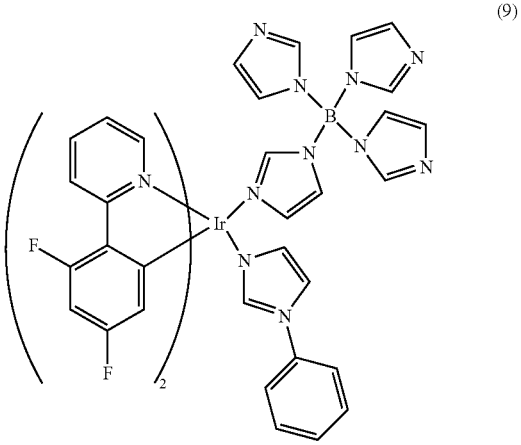

(9)

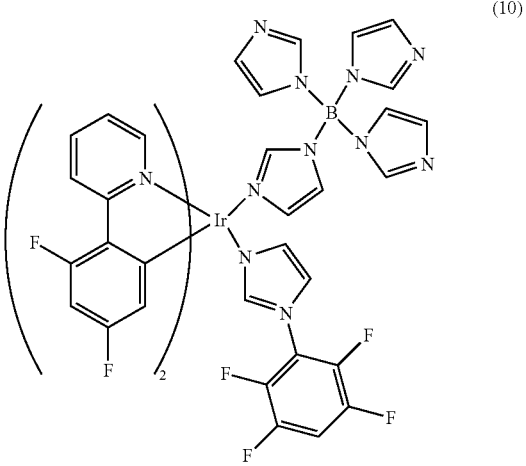

(10)

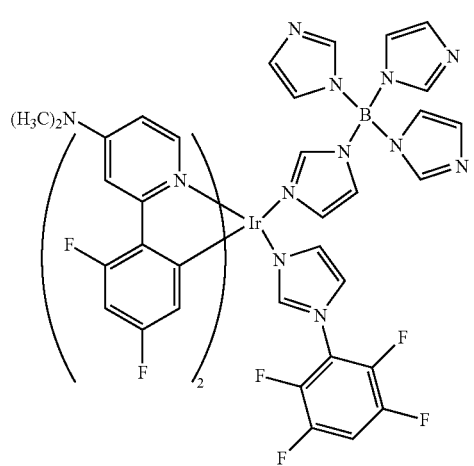
(11)
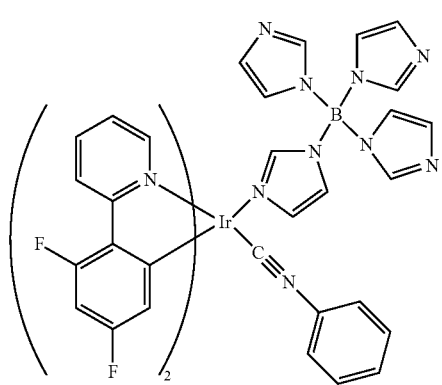
(12)
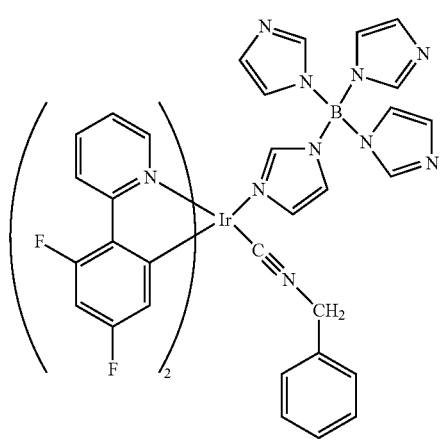
(13)
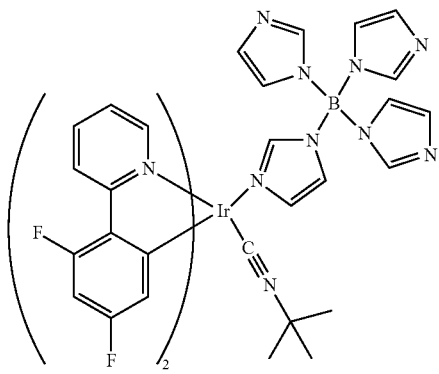
(14)
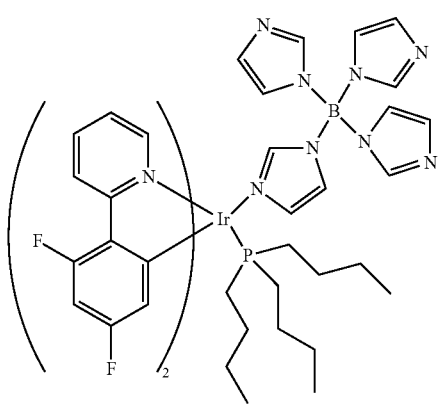
(15)
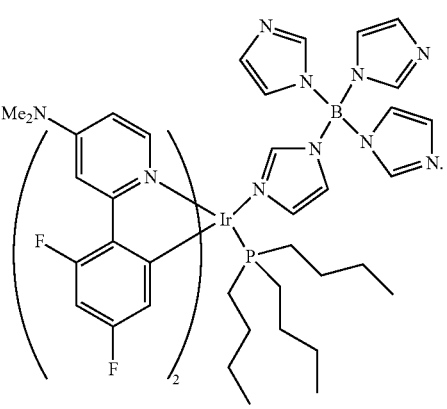
(16)
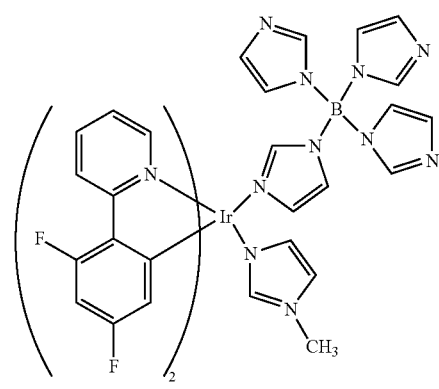
(6)

-continued (7) 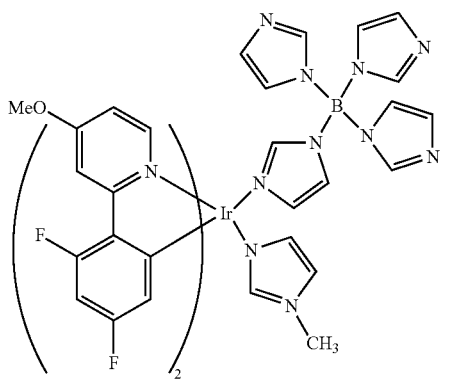

(8) 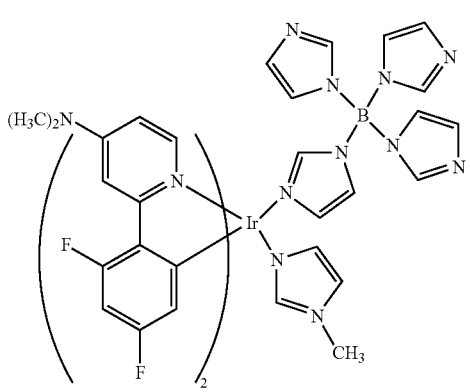

(9) 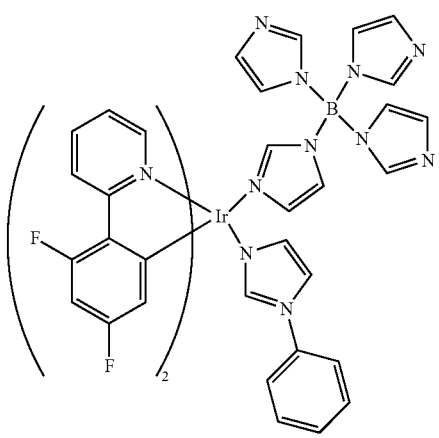

(10) 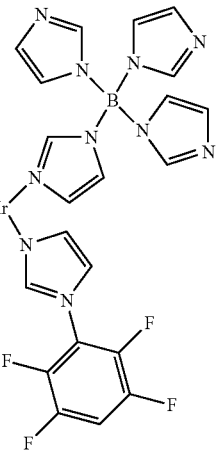

(11) 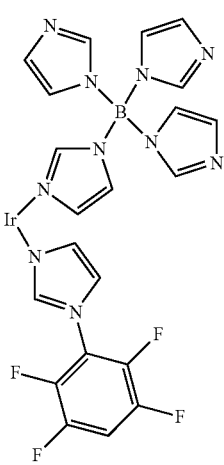

7. An organic electroluminescent device comprising an organic layer interposed between a pair of electrodes, the organic layer comprising the transition metal complex of claim 1.

8. A transition metal complex represented by Formula 1:

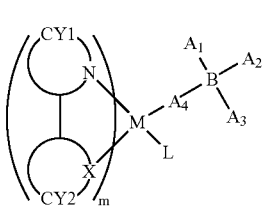

(1)

where M is a transition metal;
CY1 contains a nitrogen atom that is bonded to M, and CY2 has X that is bonded to M;
X is one of N and C;
L is a neutral ligand;
m is 1 or 2; and
$A_1$, $A_2$, $A_3$ and $A_4$ are each independently imidazole, pyrazole, a derivative of the imidazole, or a derivative of pyrazole; and
CY1-CY2 formed by CY1 and CY2 is a cyclometalated ligand represented by one of Formulae 1-(i) to 1-(xxiii):

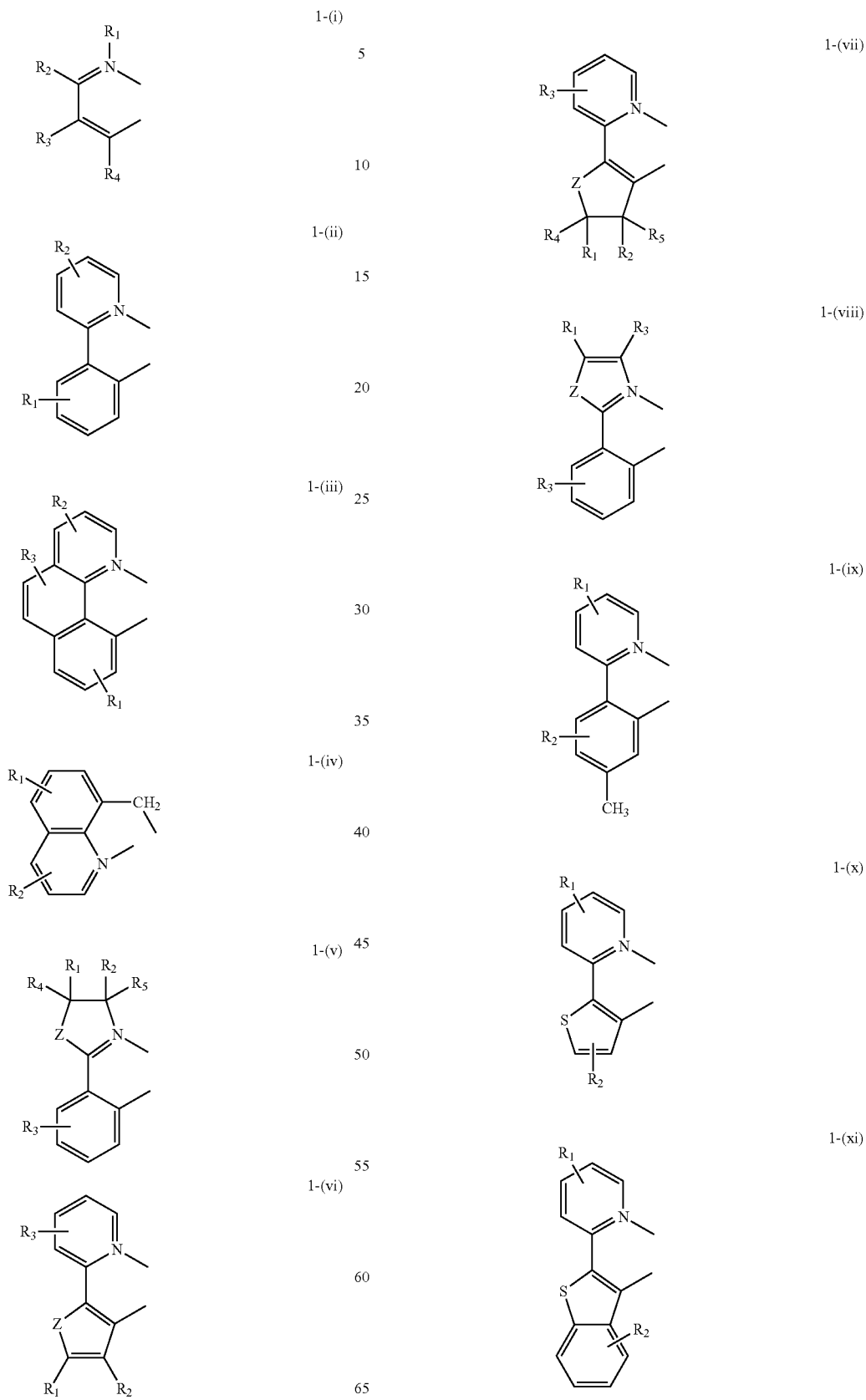

-continued
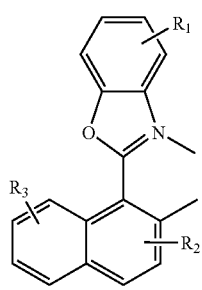
1-(xii)
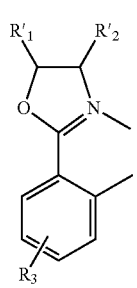
1-(xiii)
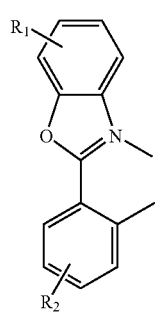
1-(xiv)
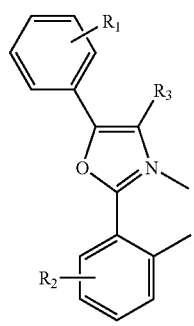
1-(xv)
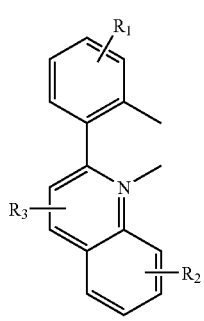
1-(xvi)
-continued
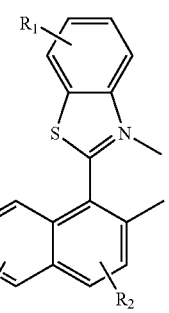
1-(xvii)
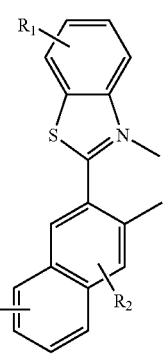
1-(xviii)
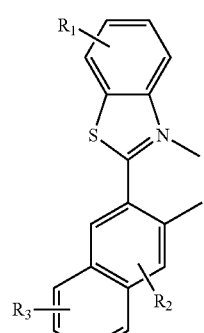
1-(xix)
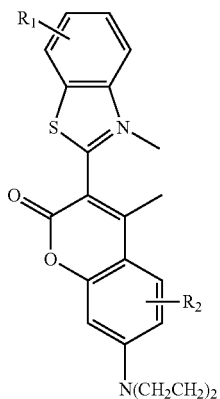
1-(xx)
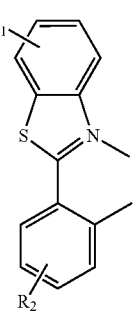

-continued 1-(xxi)
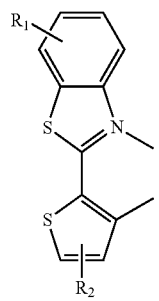

1-(xxii)
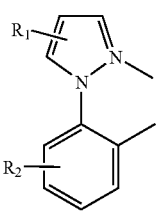

1-(xxiii)
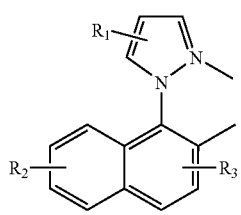

1-(xxiv)
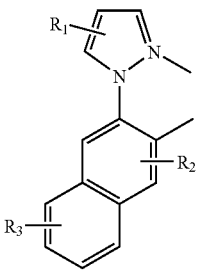

1-(xxv)
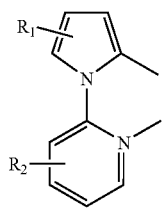

1-(xxvi)
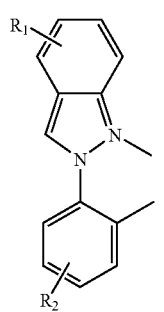

-continued 1-(xxvii)
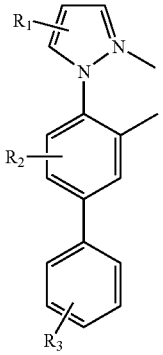

1-(xxviii)
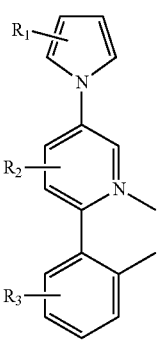

where $R_1$, $R_2$, $R_3$, $R_4$, and $R_5$ are single-substituted or multi-substituted functional groups, and $R_1$, $R_2$, $R_3$, $R_4$, and $R_5$ are each independently H, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a C1-C20 alkyl group, or a C6-C20 aryl group, where R is a substituent or a hydrogen atom.

9. The transition metal complex of claim 8, wherein L of Formula 1 is represented by one selected from the group consisting of Formulae 1-(xxix) to 1-(xxxx):

(1-(xxix))
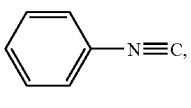

(1-(xxx))
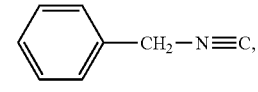

(1-(xxxi))
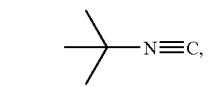

(1-(xxxii))
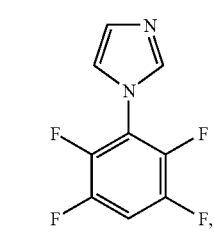

(1-(xxxiii))

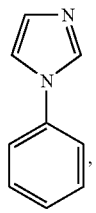

(1-(xxxiv))

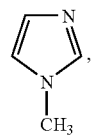

(1-(xxxv))

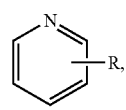

(1-(xxxvi))

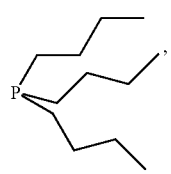

(1-(xxxvii))

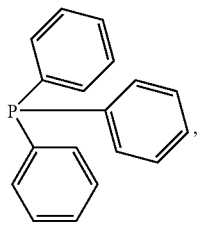

(1-(xxxviii))

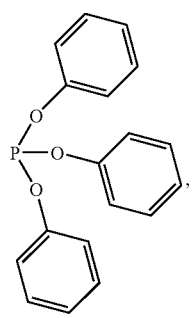

(1-(xxxix))

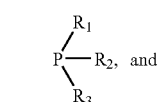

(1-(xxxx))

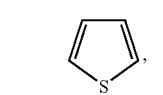

where R, $R_1$, $R_2$, and $R_3$ of Formulae 1-(xxix) to 1-(xxxx) are each independently an alkyl group, an alkoxy group, an aryl group, an aryloxy group, or a heteroaryl group.

10. An organic electroluminescent device comprising an organic layer interposed between a pair of electrodes, the organic layer composed of the transition metal complex of claim 8.

11. An organic electroluminescent device, comprising:
a pair of electrodes; and
an organic layer interposed between the pair of electrodes, the organic layer comprising an emission layer composed of the transition metal complex represented by Formula 1:

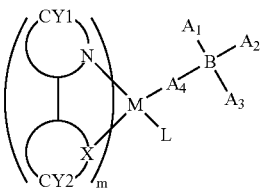

(1)

where M is a transition metal;
X is one of N and C;
L is a neutral ligand;
CY1 and CY2 are each independently an aromatic or aliphatic ring system, and CY1 has a nitrogen atom that is bonded to M, and CY2 has X that is bonded to M;
m is 1 or 2; and
$A_1, A_2, A_3,$ and $A_4$ are each independently imidazole, pyrazole, a derivative of the imidazole, or a derivative of pyrazole.

12. The organic electroluminescent device of claim 11, wherein the emission layer further comprises at least one host selected from the group consisting of at least one polymer host, a mixture of a polymer host and a low molecular weight host, a low molecular weight host, and a non-emissive polymer host.

13. The organic electroluminescent device of claim 11, wherein the emission layer further comprises a green emissive material or a red emissive material.

14. The organic electroluminescent device of claim 11, wherein the transition metal complex is represented by one of Formulae 2 and 3:

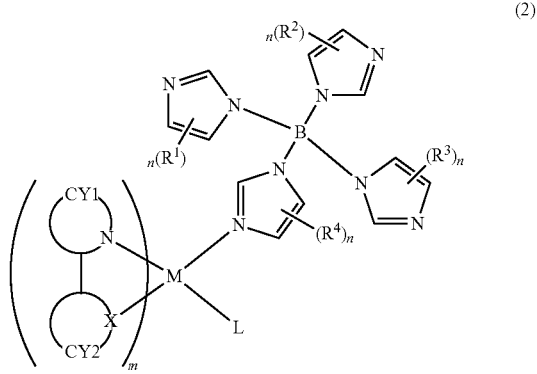

(2)

-continued

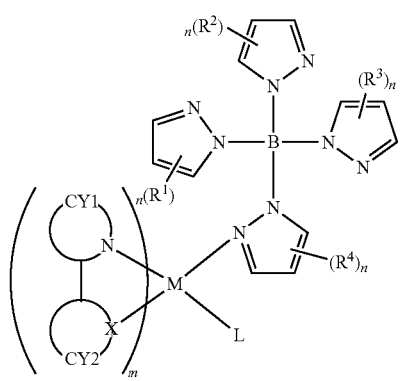
(3)

where $R^1$, $R^2$, $R^3$, and $R^4$ are each independently a substituent or H; and n is 1, 2, or 3.

15. The organic electroluminescent device of claim 11, wherein $A_1$, $A_2$, $A_3$, and $A_4$ are each independently substituted with one substituent selected from the group consisting of a hydrogen atom, an alkyl group, an alkenyl group, an alkynyl group, an aryl group, an amino group, an alkoxy group, an aryloxy group, a heterocyclicoxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclicthio group, a sulfonyl group, a sulfynyl group, an ureido group, a phosphoric acid amid group, a hydroxyl group, a mercapto group, a halogen atom, a cyano group, a sulfo group, a carboxyl group, a nitro group, a hydroxamine acid group, a sulfino group, a hydrazino group, an imino group, a heterocyclic group a silyl group, and a silyloxy group.

16. The organic electroluminescent device of claim 11, wherein the compound represented by Formula 1 is represented by Formula 5:

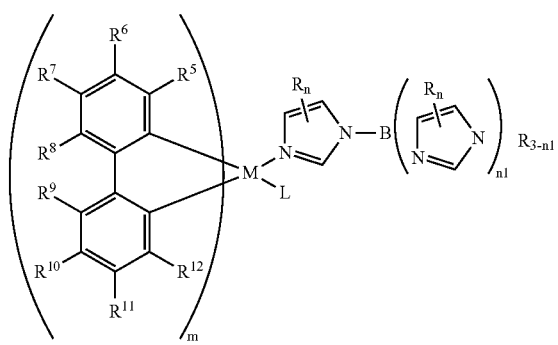
(5)

where $R^5$, $R^6$, $R^7$, $R^8$, $R^9$, $R^{10}$, $R^{11}$, $R^{12}$, R, and R' are each independently a substituent or a hydrogen atom where n is 1, 2, or 3; and n1 is 3.

17. The organic electroluminescent device of claim 11, wherein M is Ru, Rh, Os, Ir, Pt, or Au.

18. The organic electroluminescent device of claim 11, wherein the transition metal complex is represented by one of Formulae 6 through 16:

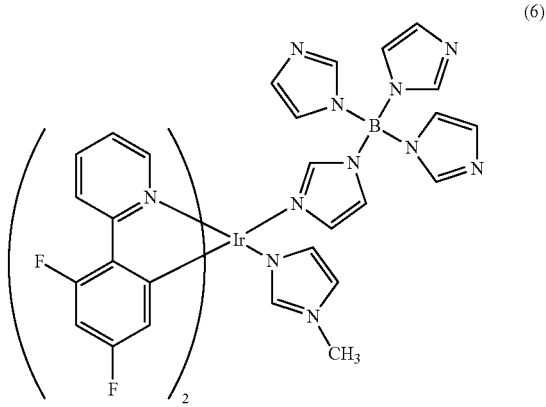
(6)

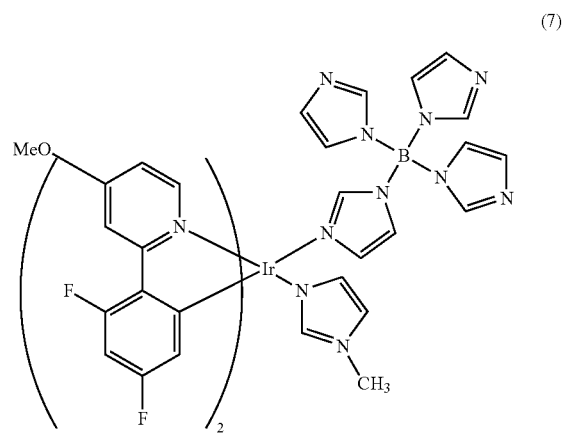
(7)

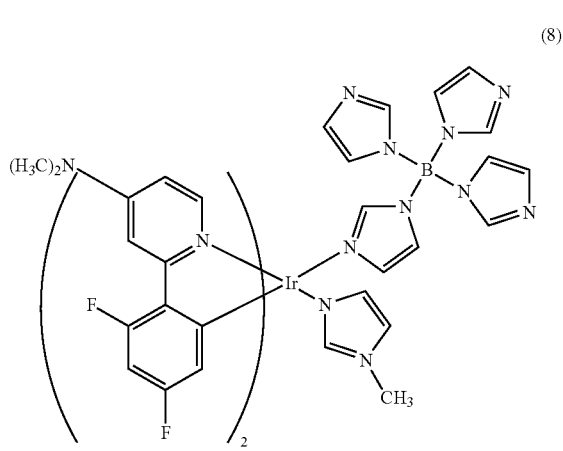
(8)

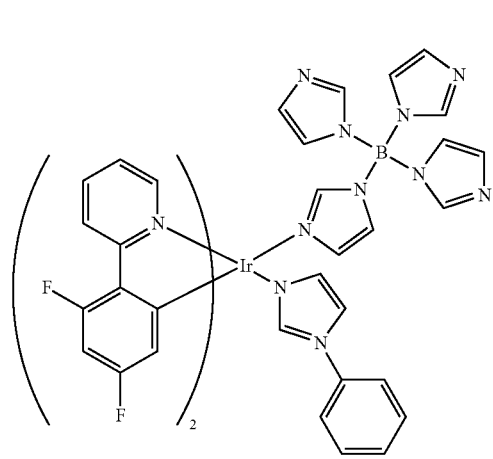
(9)
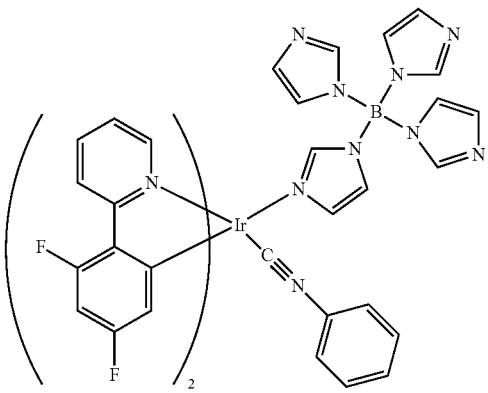
(12)
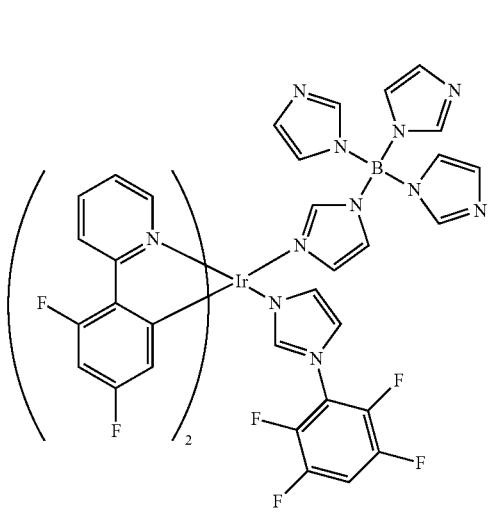
(10)
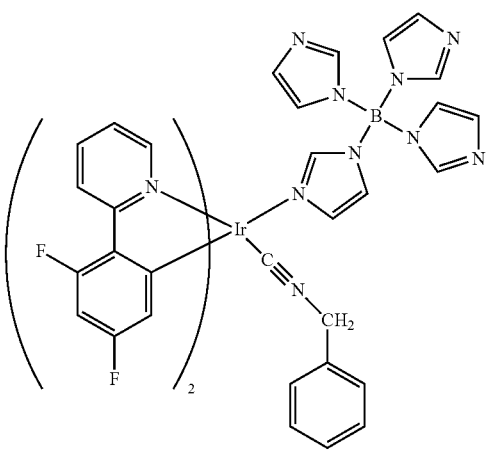
(13)
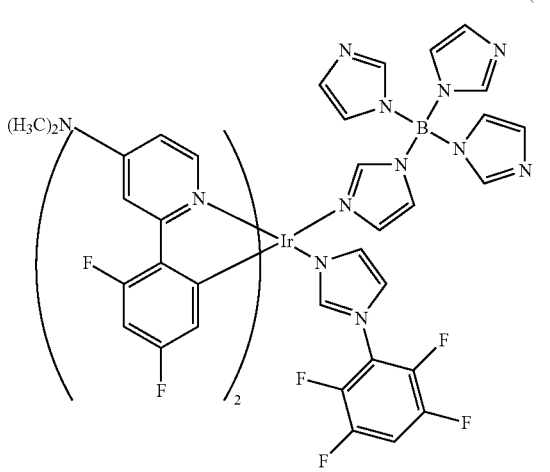
(11)
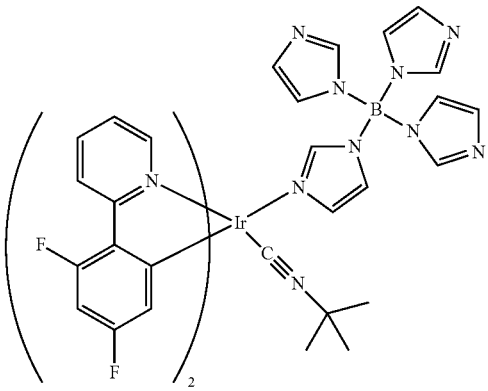
(14)

-continued
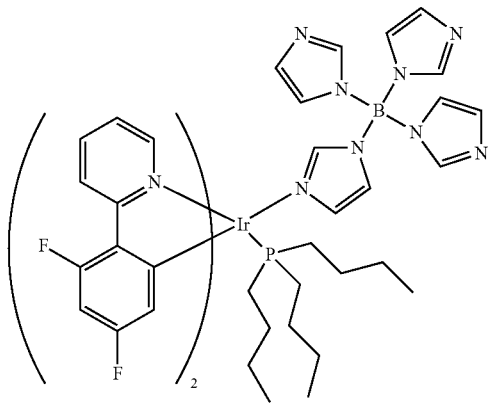
(15)
-continued
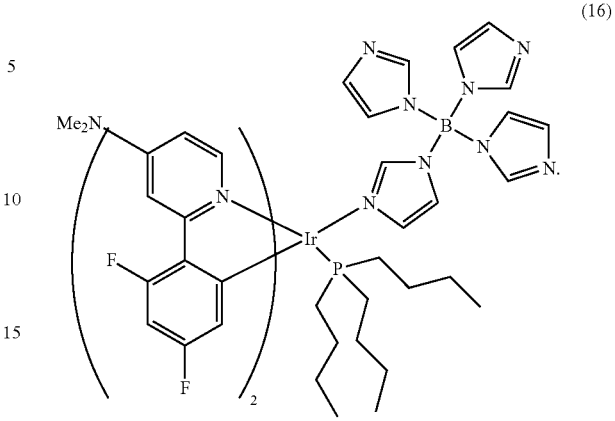
(16)
19. The organic electroluminescent device of claim 18, wherein the organic layer further comprises a green emissive material or a red emissive material.
20. The organic electroluminescent device of claim 11, wherein the organic electroluminescent device emits light of 400 nm to 650 nm.
* * * * *